United States Patent
Brodie et al.

(10) Patent No.: US 6,200,965 B1
(45) Date of Patent: Mar. 13, 2001

(54) 17-AZOLYL STEROIDS USEFUL AS ANDROGREN SYNTHESIS INHIBITORS

(75) Inventors: Angela Brodie, Fulton; Vincent C. O. Njar, Baltimore, both of MD (US)

(73) Assignee: The University of Marylsnd, Baltimore, Baltimore, MD (US)

(*) Notice: Subject to any disclaimer, the term of this patent is extended or adjusted under 35 U.S.C. 154(b) by 0 days.

(21) Appl. No.: 09/320,548

(22) Filed: May 27, 1999

Related U.S. Application Data

(62) Division of application No. 08/953,403, filed on Oct. 17, 1997.

(51) Int. Cl.$^7$ ............................. A61K 31/58; C07J 43/00
(52) U.S. Cl. ............................. 514/176; 514/284; 540/2; 540/94; 540/98; 546/61
(58) Field of Search ................................. 546/14; 540/2; 514/176, 284

(56) References Cited

U.S. PATENT DOCUMENTS

| | | | |
|---|---|---|---|
| 2,664,423 | 12/1953 | Rorig | 260/239.5 |
| 3,313,809 | 4/1967 | Clinton et al. | 260/239.5 |
| 3,317,520 | 5/1967 | Clinton | 260/239.5 |
| 5,237,064 | * 8/1993 | Bakshi et al. | 546/14 |
| 5,264,427 | 11/1993 | Brodie et al. | 514/177 |
| 5,300,294 | 4/1994 | Johnson | 424/423 |
| 5,496,556 | 3/1996 | Johnson | 424/423 |
| 5,604,213 | 2/1997 | Barrie et al. | 514/176 |
| 5,620,986 | 4/1997 | Witzel et al. | 511/284 |
| 5,637,310 | 6/1997 | Johnson | 424/423 |
| 5,721,227 | * 2/1998 | Melloni et al. | 514/172 |
| 5,741,795 | 4/1998 | Aster et al. | 514/284 |
| 5,994,334 | 11/1999 | Brodie et al. | 514/176 |

OTHER PUBLICATIONS

Njar et al, *Bioorganic & Medicinal Chemistry Letters*, 6(22):2777–2782 (1996).

Njar et al, *Steroids*, 62:468–473 (1997).

Njar et al, *J. Med. Chem.*, 39:4335–4339 (1996).

Angelastro, M.R., et al. "17β–(Cyclopropylamino)–Androst–5–En–β–lkm A Selective Mechanism–Based Inhibitor of Cytochrome P450$_{17\alpha}$ (Steroid 17α–Hydroxylase/C$_{17-20}$Lyase)", Biochem. Biophys. Res. Commun. 162:1571–1577, 1989.

Ayub, M. et al. "Inhibition of Testicular 17α–Hydroxylase and 17,20–Lyase but not 3β–Hydroxysteroid Dehydrogenase–Isomerase or 17β–Hydroxysteroid Oxidoreductase by Ketoconazole and Other Imidazole Drugs" J. Steroid Biochem. 28:521–531, 1987.

Banks, P.K. et al. "Regulation of Ovarian Steroid Biosynthesis by Estrogen during Proestrus in the Rat" Endocrinology 129:1295–1304, 1991.

Barrie, S.E. "Inhibition of 17α–Hydroxylase/C17–C20 Lyase by Bifluranol and its Analogues" J. Steroid Biochem. 33:1191–1195, 1989.

Brodie, A.M.H. et al., "Studies on the Mechanism of Estrogen Biosynthesis in the Rat Ovary–l" J. Steroid Biochem. 7:787–793, 1976.

Brodie, A.M.H. et al., "Inactivation of Aromatase In vitro by 4–Hydroxy–4–Androstene–3, 17–Dione and 4–Acetoxy–4–Androstene–3, 17–Dione and Sustained Effects in vivo" Steroids, 38:693–702, 1981.

Brodie, A.M.H., et al. "Lack of Evidence for Aromatase in Human Prostatic Tissues: Effects of 4–Hydroxyandrostenedione and Other Inhibitors on Androgen Metabolism" Cancer Research, 49:6551–6555, 1989.

Brodie, A.M.H. "Inhibitors of Steroid Biosynthesis" (Ch. 16). in Design of Enzyme Inhibitors as Drugs, vol. 2, (Eds) M. Sandler and H.J. Smith, Oxford University Press, pp. 503–522, 1993.

Brodie, A.M.H. "Steroidogenesis Pathway Enzymes—Introduction" (Ch. 9) in Design of Enzyme Inhibitors as Drugs vol. 2, (Eds) M. Sandler and H.J. Smith, Oxford University Press, pp. 1–13, 1993.

Brodie, A.M.H. "Steroidogenesis Pathway Enzymes—Aromatase Inhibitors" (Section 9B) in Design of Enzyme Inhibitors as Drugs vol. 2, (Eds) M. Sandler and H.J. Smith, Oxford University Press, pp. 424–438, 1993.

Bruchovsky, N. et al. "The Conversion of Testosterone to 5 α–Androstan–17α–of–3–one by Rat Prostate in Vivo and in Vitro" J. Biol. Chem. 243:2012–2021, 1968.

Bulun et al., "Use of Tissue–Specific Promoters in the Regulation of Aromatase Cytochrome P450 Gene Expression in Human Testicular and Ovarian Sex Cord Tumors, as well as in Normal Fetal and Adult Gonads" J. Clin. Endocrinol. Metab. 77:1616–1621, 1993.

Chomczynski, P. et al. "Single–Step Method of RNA Isolation by Acid Guanidinium Thiocyanate–Phenol–Chloroform Extraction" Anal. Biochem. 162:156–159, 1987.

Church, G.M. et al. "Genomic Sequencing" Proc. Soc. Natl. Acad. Sci. 81:1991–1995, 1984.

Cohen, S.M. et al. "Comparison of the Effects of New Specific Azasteroid Inhibitors of Steroid 5α–Reductase on Canine Hyperplastic prostate: Suppression of Prostatic DHT Correlated with prostate Regression" The Prostate 26:5571, 1995.

Coen, P., et al. "An Aromatase–Producing Sex–Cord Tumor Resulting in Prepubertal Gynecomastia" New Eng. J. Med 324:317–322, 1991.

(List continued on next page.)

Primary Examiner—Mukund J. Shah
Assistant Examiner—Pavanaram K Sripada
(74) Attorney, Agent, or Firm—Sughrue, Mion, Zinn, Macpeak & Seas, PLLC

(57) ABSTRACT

Androgen synthesis inhibitors, as well as methods for the use of the same to reduce plasma levels of testosterone and/or dyhydrotestosterone, and to treat prostate cancer and benign prostatic hypertrophy, are disclosed.

7 Claims, 10 Drawing Sheets

OTHER PUBLICATIONS

Coombes, R.C. et al. "4–Hydroxy Androstenedione Treatment for Postmenopausal Patients with Advanced Breast Cancer" Steroids 50:245–252, 1987.

Covey, D.F. et al., "10β–Propynyl–substituted Steroids" J. Biol. Chem., 256:1076, 1980.

Crawford, E.D. et al. "A Controlled Trial of Leuprolide with and without Flutamide in Prostatic Carcinom" N. Engl. J. Med., 321:419–424, 1989.

di Salle, E. et al. "Effects of 5α–Reductase Inhibitors on Intraprostatis Androgens in the Rat" J. Steroid Biochem. Mol. Biol., 53, 1–6:381–385, 1995.

Doorenbos, N.J. et al. "17β–Isoxazolyl and 17β–Pyrazolyl Steroids from 3β–Hydroxy–21–formylpregn–5–en–20–one." J. Org. Chem., 31:3193, 1966.

Forti, G., et al. "Three–Month Treatment with a Long–Acting Gonadotropin–Releasing Hormone Agonist of Patients with Benign prostatic Hyperplasia: Effects on Tissue Androgen Concentration, 5α–Reductase Activity and Androgen Receptor Content" J. Clin. Endocrinol. Metab. 68:461–468, 1989.

Frye, S. et al. "6–Azasteroids; Potent Dueal Inhibitors of Human Type 1 and 2 Steroid 5α–Reductase" J. Med. Chem. 36:4313–4315, 1993.

Gaddipati, J.P. et al. "Frequent Detection of Codon 877 Mutation in the Androgen Receptor Gene in Advanced Prostate Cancers" Cancer Res. 54:2861–2864, 1994.

Geller, J. et al. "Comparison of Prostatic Cancer Tissue Dihydrotestosterone Levels at the Time of Relapse Following Orchiectomy or Estrogen Therapy" J. Urology 132:693–696, 1984.

Gold, R. et al. "Detection of DNA Fragmentation in Apoptosis: Application of in situ Nick Translation to Cell Culture Systems and Tissue Sections" J. Histochem. Cytochem. 41,7:1023–1030, 1993.

Goldman, A.S. et al. "Production of Male Pseudohemaphroditism in Rats by Two New Inhibitors of Steroid 17α–hydroxylase and C17–20 Lyase" J. Endoc. 71:289, 1976.

Gormley, G.J. "Role of 5α–Reductase Inhibitors in the Treatment of Advanced Prostatic Carcinoma" Urol. Clinics of North America 18, 1:93–97, 1991.

Goss, P.E. et al. "Treatment of Advanced Postmenopausal Breast Cancer with an Aromatase Inhibitor, 4–Hydroxyandrostenedione: Phase II Report" Cancer Res. 46:4223–4826, 1986.

Goya, S. et al. "Studies on Cardiotonic Steroid Analogs" Yakugaku Zasshi., 90:537, 1970.

Haaase–Held, M., et al. "The Synthesis of 4–Cyanoprogresterone: A Potent Inhibitor of the Enzyme 5–α–Reductase" J. Chem. Soc. Perkin Trans. 1:2999, 1992.

Habernicht, U.F. et al. "Induction of Estrogen–Related Hyperplastic changes in the Prostate of the Cynomolgus Monkey (Macaca fascicularis) by Androstenedione and its Antagonization by the Aromatase Inhibitor 1–Methyl–Androsta–1, 4–Diene–3, 17–Dione" Prostate, 11:313–326, 1987.

Haffner, "Synthesis of 6–Azacholesten–3–ones:Potent Inhibitors of 5α–Reductase"; Tetrahedron Letters 36:4039–4042, No. 23, 1995.

Hamilton, G.A. "Chemical Models and Mechanisms for Oxygenases" in "Molecular Mechanism of Oxygen Activation"; Hayishi, O., Ed.; Academic Press: New York: 405, 1974.

Harada, "Novel Properties of Human Placental Aromatase as Cytochrome P–450: Purification and Characterization of a Unique Form of Aromatase", J. Biochem 103:106–113 (1988).

Henderson, D. "Estrogens and Benign prostatic Hyperplasia: Rationale for Therapy with Aromatase Inhibitors" Annals med. 23:201–203, 1991.

Hoehn, W., et al. "Human Prostatis Adenocarcinoma:Some Characteristics of a Serially Transplantable Line in Nude Mice (PC82)" Prostate 1:94–104, 1980.

Holt, D.A. et al. "Inhibition of Steroid 5 –Reductase by Unsaturated 3–Carboxysteroids" J. Med. Chem. 33:943–950, 1990.

Hsiang, Y.H.H. et al. "The influence of 4–Hydroxy–4–Androstene–3, 17–Dione on Androgen Metabolixm and Action in Cultured Human Foreskin Fibroblasts" J. Steroid Biochem. 26:131–136, 1987.

Huynh, C. et al. "Fixation d'un Groupe Nitrile en Position 4 des Céto–3$_{A}$⁴–Stéroides" Bull. Soc. Chim. Fr.: 4396, 1971.

Inkster et al "Human Testicular Aromatase:Immunocyctochemical and Biochemical Studies" J. Clin. Endocrinol. Metab. 80:1941–1947, 1995.

Ishibashi, K. et al. "Synthesis of B–NOR–4–AZA–5α–Androstane Compound as 5α–Reductase Inhibitor" Bioorg. & Med. Lett., 4:729–732, 1994.

Jarman, M., et al. "Hydroxyperfluorozobenzenes: Novel Inhibitors of Enzymes of Androgen Biosynthesis" J. Med. Chem. 33:2452–2455, 1990.

Kitz, R. et al., "Esters of Methanesulfonic Acid as Irreversible Inhibitors of Acetylcholinesterase" J. Biol. Chem. 237: 3245–3249, 1962.

Klus, G. et al. "Growth Inhibition of Human Prostate Cells in Vitro by Novel Inhibitors of Androgen Synthesis" 5th Int'l Cong. on Hormones & Cancer, Abst. 83, 1995.

Kozak, I., et al. "Nuclei of Stroma: Site of Highest Estrogen Concentration in Human Benign Prostatic Hyperplasia" Prostate 3:433–438, 1982.

Krieg, M., et al. "Stroma of Human Benign Prostatic Hyperplasia: Preferential Tissue for Androgen Metabolism and Oestrogen Binding" Acta Endocri. (Copenh.) 96:422–432, 1981.

Kyprianou, N., et al. "Programmed Cell Death During Regression of PC–82 Human Prostate Cancer following Androgen Ablation" Cancer Research 50:3748–3753, 1990.

Kyprianou, N. et al. "Expression of Transforming Growth Factor–β in the Rat Ventral Prostate during Castration–Induced Programmed Cell Death" Mol. Endocrin. 3:1515–1522, 1989.

Labrie, F. et al. "Combination Therapy for Prostate Cancer" Cancer Suppl. 71:1059–1067, 1993.

Li, J., et al. "4–Pregnene–3–One–209–Carboxaldehyde: A Potent Inhibitor of 17α–Hydroxylase/$C_{17,20}$–Lyase and of 5α–Reductase" J Steroid Biochem. Mol. Biol. 42:313–321, 1992.

Li, J. et al. "Inhibition of Androgen Synthesis by 22–Hydroximino–23,24–Bisnor–4–Cholen–3–One" The Prostate, 26:140–150, 1995.

Li, J. et al. "Synthesis and evaluation of pregnane derivatives as inhibitors of human testicular 17α–hydroxylase/$C_{17,20}$–lyase" J. Med. Chem. 39:4335–4339, 1996.

Lu Q., et al. "Expression of Aromatase Protein and Messenger Ribonucleic Acid in Tumor Epithelial Cells and Evidence of Functional Significance of Locally Produced Estrogen in Human Breast Cancers" *Endocrinology* 137:3061–3068, No. 7, 1996.

Mawhinney, M.G. et al. "Androgens and Estrogens in Prostatic Neoplasia" Adv. Sex Horm Res 2:41–209, 1976.

McCague, R. et al. "Inhibition of Enzymes of Estrogen and Androgen Biosynthesis by Esters of 4–Pyridylacetic Acid" J. Med. Chem. 33:3050–3055, 1990.

McDonald, I.A., et al. "Inhibition of Steroid 5α–Reductase by 'Inverted,' Competitive Inhibitors" Bioorg. & Med. Lett. 4: 847–851, 1994.

Metcalf, B.W., et al. "Substrate–Induced Inactivation of Aromatase by Allenic and Acetylenic Steroids" J. Am. Chem. Soc. 103: 3221, 1981.

Nakajin, S. et al. "Microsomal Cytochrome P–450 from Neonatal Pig Testis" J. Biol. Chem. 256:3871–3876, 1981.

Nakajin, S., et al. "Microsomal Cytochrome P–450 from Neonatal Pig Testis: Two Enzymatic Activities (17α–Hydroxylase and $C_{17,20}$–Lyase) Associated with One Protein" Biochem. 20:4037–4042, 1981.

Nakajin, S. et al. "Inhibitory Effects and Spectral Changes on Pig Testicular Cytochrome P–450(17α–Hydroxylase/Lyase) by 20β–Hydrox–$C_{21}$–Steroids" Yakugaku Zasshi (Japan), 108:1188–1195, 1988.

Njar, V.C.O., et al. "Novel 10β–Aziridinyl Steroids; Inhibitors of Aromatase" J. Chem. Soc. Perkin Trans 1: 1161, 1993.

Njar et al., "Nucleophilic Vinylic 'Addition–Elimination' Substitution Reaction of 3B–Acetoxy–17–Chloro–16–Formylandrosta–5,16–Diene: A Novel and General Route to 17–Substituted Steroids" Bioorganic and Medical Chemistry Letters 6: 2777–2782, 1996, No. 22.

Onoda, M. et al. "Affinity Alkylation of the Active Site of $C_{21}$ Steroid Side–Chain Cleavage Cytochrome P–450 from Neonatal Porcine Testis: A Unique Cysteine Residue Alkylated by 17–(Bromoacetoxy) progesterone" Biochemistry, 26: 657, 1987.

Pataki, J., et al. "Synthesis of Fluorinated 3β–Hydroxypregn–5–EN–20–One Derivatives" Steroid, 28: 437–447, 1976.

Pelc, B., et al. "Androstane Derivatives Substituted by Pyrazole Ring in Positive 17" Coflection Czechoslov, Chem. Commun., 34: 442, 1969.

Petrow, V., et al. "Studies on a 5α–Reductase Inhibitor and Their Therapeutic Implications" The Prostatic cell: Structure and Function Part B: 283–297, 198 1, Alan R. Liss Inc., 150 Fifth Avenue, New York, NY 10011.

Potter G.A., et al. "Novel Steroidal inhibitors of Human Cytochrome P45017,,(1 7α–Hydroxylase–$C_{17,20}$–lyase): Potential Agents for the Treatment of Prostatic Cancer" J. Med. Chem. 38: 2463–2471, 1995.

Rasmusson, G.H., et al. "Azasteroids: Structure–Activity Relationships for Inhibition of 5α–Reductase and of Androgen Receptor Binding" J. Med. Chem. 29:2298–2315, 1986.

Rasmusson, G.H., et al. "Azasteroids as Inhibitors of Rat Prostatic 5α–Reductase" J. Med. Chem. 27: 1690–1701, 1984.

Rittmaster, R.S., et al. "Differential Effect of 5α–Reductase Inhibition and Castration on Androgen–Regulated Gene Expression in Rat Prostate" *Mol. Endocrin.* 5:1023–1029, 1991.

Russell, D.W., et al. "Steroid 5α–Reductase: Two Genes/Two Enzymes" Ann. Rev. Biochem. 63:25–61, 1994.

Schieweck, K., et al. "Anti–Tumor and Endocrine Effects of Non–Steroidal Aromatase Inhibitors on Estrogen–Dependent Rat Mammary Tumors" J. Steroid Biochem. *Mol. Biol.* 44:633–636, 1993.

Schwarzel, W.C., et al. "Studies on the Mechanism of Estrogen Biosynthesis. VIII. The Development of Inhibitors of the Enzyme System in Human Placenta" Endocrinology 92:866–880, 1973.

Shao, T. C., et al. "Effects of Finasteride on the Rat Ventral Prostate" *J. Androl.* 14:79–86, 1993.

Shearer, R. et al. "Studies in Prostatic Cancer with 4–Hydroxyandrostenedione" In: Coombes, R.C. and Dowsett, M. (eds.), 4–hydroxyandrostenedione—A new approach to hormone–dependent cancer.pp. 41–44, 1991.

Sjoerdsma, A. "Suicide Enzyme Inhibitors as Potential Drugs" Clin. Pharmacol. Ther. 30:3, 1981.

Snider, C.E., et al. "Covalent Modification of Aromatase by a Radiolabeled Irreversible Inhibitors" J. Steroid Biochem. 22: 325, 1985.

Stoner, E. "The Clinical Development of a 5r–Reductase Inhibitor, Finasteride" J. Steroid Biochem. Molec. Biol. 37:375–378, 1990.

Trachtenberg, J. "Ketoconazole Therapy in Advanced Prostatic Cancer" J. Urol. 132:61–63, 1984.

Van Steenbrugge, G.J., et al. "Transplantable Human Prostatic Carcinoma (PC–82) in Athymic Nude Mice III. Effects of Estrogens on the Growth of the Tumor Tissue" Prostate 12:157–171, 1988.

Veldscholte, J., et al. "Anti–Androgens and the Mutated Androgen Receptor of LNCaP Cells; Differential Effects on Binding Affinity, Heat–Shock Protein Interaction, and Transcription Activation" Biochemistry 31:2393–2399, 1992.

Vescio R.A., et al. "Cancer Biology for Individualized Therapy: Correlation of Growth Fraction Index in Native–State Histoculture with Tumor Grade and Stage" Proc Natl Acad Sci USA 87: 691–695, 1990.

Visakorpi, T., et al. "In vivo Amplification of the Androgen Receptor Gene and Progression of Human Prostate Cancer" Nature Genetics 9: 401–406, 1995.

Wainstein M.A., et al. "CWR22: Androgen–dependent Xenograft Model Derived from a Primary Human Prostatic Carcinoma" Cancer Res. 54:6049–6052, 1994.

Weintraub, P.M., et al. Merrel Dow Pharmaceuticals Inc., EP 0: 469–548 A2, 1991. (Abstract).

Weintraub, P.M., et al. Merrel Dow Pharmaceuticals Inc., CA 116: 214776v, 1992 (EP0469–547). (Abstract).

Williams, G., et al. "Objective Responses to Ketoconazole Therapy in Patients with Relapsed Progressive Prostatic Cancer" Br. J. Urol. 58: 45–51, 1986.

Yue, W., et al. "A New Nude Mouse Model for Postmenopausal Breast Cancer Using MCF–7 Cells Transfected with the Human Aromatase Gene" Cancer Res. 54:5092–5095, 1994.

Yue, W., et al. "Effect of Aromatase Inhibitors on Growth of Mammary Tumors in a Nude Mouse Model" Cancer Res. 55: 3073–3077, 1995.

Zhou, J.L., et al. "The Effect of Aromatase Inhibitor 4–Hydroxyandrostenedione on Steroid Receptors in Hormone–Dependent Tissues of the Rat" J. Steroid Biochem. *Mol. Biol.* 52:71 76, 1995.

Yang–zhi Ling et al., (1997), "17–Imidazolyl, pyrazolyl, and isoxazolyl androstene derivatives. Novel steroidal inhibitors of human cytochrome C17,20–lyase (P450$_{17\alpha}$)", J. Med. Chem. 40(20):3297–3304.

Njar et al., (1999), "Inhibitors of 17α–hydroxylase/17, 20–lyase (CYP17): Potential agents for the treatment of prostate cancer", Current Pharmaceutical Design, 5:163–180.

Brian J. Long et al., (1999), "Effects of novel inhibitors of androgen synthesis on the growth of human prostate cancer in vitro and vivo", (manuscript).

Grigoryev et al., (1999), "Cytochrome P450c17–expressing *Escherichia coli* as a first–step screening system system for 17α–hydroxylase–C$_{17,20}$–lyase inhibitors", Anal. Biochem., 267:319–330.

Njar et al., "Nucleophilic Vinylic "Addition–Elimination" Substitution Reaction of 3β–Acetoxy–17–Chloro–16–Formylandrosta–5,16–Diene: A Novel and General Route to 17–Substituted Steroids.Part 1—Synthesis of Novel 17–Azoly–Δ$^{16}$ Steroids; Inhibitors of 17α–Hydroxylase/17,20–Lyase (17α–Lyase)", Bioorganic and Medicinal Chem., vol. 6, No. 22, pps 2777–2782 (1996).

Rasmusson et al., "Therapeutic Control of Androgen Action", Annual Reports in Med Chem Acad. Press, chapter 23, pp. 225–232 (1994).

Szendi et al., "Steroids, LIII: New Routes of Aminosteroids [1]", Monatschefte Fur Chemia Chemical Monthly, 127:1189–1196(1996).

Vakathar et al., Chem. Ind. (London) 17, 742 (1977) (Abstract).

Pappo et al., "The Synthesis of 2–Azasteroids", Tetrahedron Letters, 31:3237–3240 (1972).

Frye et al., "Structure–Activity Relationships for Inhibition of Type 1 and 2 Human 5α–Reductase and Human Adrenal 3β–Hydroxy–Δ$^5$–steroid Dehydrogenase/3–Keto–Δ$^5$–steroid Isomerase by 6–Azaandrost–4–en–3–ones: Optimization of the C17 Substituent", J. Med. Chem. 38:2621–2627(1995).

Guarna et al., "A Concise Route to 19–Nor–10–azasteroids, a New Class of Steroid 5α–Reductase Inhibitors. 3. Synthesis of (+)–19–Nor–10–azatestosterone and (+)–17β–(Acetyloxy)–(5β–)–10–azaestr–1–en–3–one", J. Org. Chem. 63:4111–4115 (1998).

Frye et al., "6–Azasteroids: Structure–Activity Relationship for Inhibition of Type 1 and 2 Human 5α–Reductase and Human Adrenal 3β–Hydroxy–Δ$^5$ Steroid Dehydrogenase/3–Keto–Δ$^5$–steroid Isomerase", J. Med. Chem. 37:2352–2360 (1994).

* cited by examiner $Km = 0.56 \mu M$ $V\ max = 42$ pmol/min/mg protein

17-AZOLYL STEROIDS USEFUL AS ANDROGREN SYNTHESIS INHIBITORS

This is a divisional of application Ser. No. 08/953,403 filed Oct. 17, 1997.

The development of the present invention was supported by the University of Maryland, Baltimore, Md. and by funding from the National Institutes of Health under grant number CA 27440. The United States Government has a non-exclusive, irrevocable, paid-up license to practice or have practiced for or on behalf of the United States the invention herein as provided for by the terms of the above mentioned contracts awarded by the United States Government.

FIELD OF THE INVENTION

The present invention relates to novel 17-azolyl steroids which are useful as androgen synthesis inhibitors, as well as methods for the use of the same to reduce plasma levels of testosterone and/or dyhydrotestosterone, and to treat prostate cancer and benign prostatic hypertrophy.

BACKGROUND OF THE INVENTION

Breast cancer kills 45,000 women per year. In addition, prostate cancer now ranks as the most prevalent cancer in men. Approximately 160,000 new cases are diagnosed with prostate cancer each year. Of these, 35,000 will die of metastatic disease.

It has been proposed that selective aromatase (estrogen synthetase) inhibitors to control estrogen production would be useful agents for treatment of breast cancer in women (Bolla et al, *N. Eng. J. Med.,* 337:295–300 (1997)). In addition, in men, aromatase inhibitors may be useful for conditions associated with estrogen excess, such as gynecomastia and oligospermia (Coen et al, *New Eng. J. Med.,* 324:317–322 (1991); and Hsiang et al, *J. Steroid Biochem.,* 26:131–136 (1987)). It has also been suggested that aromatase inhibitors might be useful in the treatment of prostatic cancer and benign prostatic hypertrophy (BPH) (Henderson, *Annals Med.,* 23:201–203 (1991)).

Compounds which are potent and selective inhibitors of aromatase have been reported (Schwarzel et al, *Endocrinol.,* 92:866–880 (1973)). The most active of those inhibitors, 4-hydroxyandrostene-3,17-dione (4-OHA) (Brodie et al, *J. Steroid Biochem.,* 7:787–793 (1976)), was found to act by rapid competitive inhibition, followed by inactivation of the enzyme in vitro, which appeared to be long-lasting or irreversible (Brodie et al, *Steroids,* 38:693–702 (1981)). Enzyme inhibitors with these properties are thought to bind to the active site of the enzyme, are likely to be quite specific, and should have long-lasting effects in vivo due to inactivation of the enzyme (Sjoerdsma, *Clin. Pharmacol. Ther.,* 30:3 (1981)). It was also demonstrated that 4-OHA reduces peripheral plasma estrogen levels, and causes significant regression of breast cancers in postmenopausal patients with advanced metastatic disease who have relapsed from other hormonal treatment, such as ovariectomy and tamoxifen. 4-OHA has both oral and parenteral activity, and is without significant side-effects in these patients (Goss et al, *Cancer Res.,* 46:4223–4826 (1986); and Coombes et al, *Steroids,* 50:245–252 (1987)). 4-OH-A, also known as formastane, was approved in 1995 for the treatment of breast cancer in many countries worldwide, including most European countries and Canada. It was the first new treatment for breast cancer in 10 years.

In men, estrogens are produced by the testes, and by peripheral aromatization of adrenal androgens. Testosterone is the major product of the testis, and is converted in the prostate by 5α-reductase to the more potent androgen, dihydrotestosterone (DHT) (Bruchovsky et al, *J. Biol. Chem.,* 243:2012–2021 (1968)). While androgens are of primary importance in the growth of normal prostate, BPH and prostatic cancer, several lines of evidence suggest that estrogens may also have a role (Mawhinney et al, *Adv. Sex Horm. Res.,* 2:41–209 (1976)).

4-OHA also inhibits 5a-reductase in vitro, although with less potency than it inhibits aromatase (Brodie et al, *Cancer Res.,* 49:6551–6555 (1989b)). Because of these two activities, the possibility that 4-OHA might be effective in prostatic cancer was explored in a small group of men with advanced disease. Subjective responses were observed in 80% of these patients, although there was no clear evidence of objective remissions (Shearer et al, *In: 4-hydroxyandrostenedione—A New Approach to Hormone-Dependent Cancer,* Eds. Coombes et al, pages 41–44 (1991)). Estrogen levels were reduced as expected but, DHT concentrations were unchanged in the patients. The latter finding, in addition to the weak androgenic activity of 4-OHA, may have determined the lack of objective responses.

Chemotherapy is usually not highly effective, and is not a practical option for most patients with prostatic cancer because of the adverse side-effects which are particularly detrimental in older patients. However, the majority of patients initially respond to hormone ablative therapy (McGuire, In: *Hormones and Cancer,* Eds. Iacobelli et al, Raven Press, New York, Vol. 15, pages 337–344 (1980)) although they eventually relapse, as is typical with all cancer treatments. Current treatment by orchidectomy or administration of gonadotropin-releasing hormone (GnRH) agonists result in reduced androgen production by the testis, but does not interfere with androgen synthesis by the adrenals. Following 3 months of treatment with a GnRH agonist, testosterone and DHT concentrations in the prostate remained at 25% and 10%, respectively, of pretreatment levels (Forti et al, *J. Clin. Endocrinol. Metab.,* 68:461–468 (1989)). Similarly, about 20% of castrated patients in relapse had significant levels of DHT in their prostatic tissue (Geller et al, *J. Urol.,* 132:693–696 (1984)). These finding suggest that the adrenals contribute precursor androgens to the prostate. This is supported by clinical studies of patients receiving combined treatment with either GnRH or orchidectomy and an anti-androgen, such as flutamide, to block the actions of androgens, including adrenal androgens. Such patients have increased progression-free survival time compared to patients treated with GnRH agonist or orchidectomy alone (Crawford et al, *N. Engl. J. Med.,* 321:419–424 (1989); and Labrie et al, *Cancer Suppl.,* 71:1059–1067 (1993)).

Although patients initially respond to endocrine therapy, they frequently relapse. It was reported recently that in 30% of recurring tumors of patients treated with endocrine therapy, high-level androgen receptor (AR) amplification was found (Visakorpi et al, *Nature Genetics,* 9:401–406 (1995)). Also, flutamide tends to interact with those mutant AR, and stimulate prostatic cell growth. This suggests that AR amplification may facilitate tumor cell growth in low androgen concentrations. Thus, total androgen blockade as first line therapy may be more effective than conventional androgen deprivation by achieving maximum suppression of androgen concentrations which may also prevent AR amplification. It is presently unclear whether sequential treatment with different agents can prolong the benefits of the initial therapy. This strategy has been found effective in breast cancer treatment. New agents which act by different mechanisms could produce second responses in a portion of relapsed patients. Although the percentage of patients who respond to second-line hormonal therapy may be relatively low, a substantial number of patients may benefit because of the high incidence of prostatic cancer. Furthermore, there is the potential for developing more potent agents than current therapies, none of which are completely effective in blocking androgen effects.

Human cytochrome 17α-hydroxylase/$C_{17,20}$-lyase (hereinafter "$P450_{17\alpha}$") is a key enzyme in the biosynthesis of androgens, and converts the $C_{21}$ steroids (pregnenolone and progesterone) to the $C_{19}$ androgens, dehydroepiandrosterone (DHEA), 5-androstenediol (A-diol), testosterone, and 5 androstenedione in the testis and adrenals. Some inhibitors of $P450_{17\alpha}$ have been described (Barrie, *J. Steroid Biochem.*, 33:1191–1195 (1989); McCague et al, *J. Med. Chem.*, 33:3050–3055 (1990); Jarman et al, *J. Med. Chem.*, 33:2452–2455 (1990); Ayub et al, *J. Steroid Biochem.*, 28:521–531 (1987); Nakajin et al, *Yakugaku Zasshi. (Japan)*, 108:1188–1195 (1988); Nakajin et al, *Chem. Pharm. Bull. (Tokyo)*, 37:1855–1858 (1989); Angelastro et al, *Biochem. Biophys. Res. Commun.*, 162:1571–1577 (1989); Potter et al, *J. Med. Chem.*, 38:2463–2471 (1995); and Rowlands et al, *J. Med. Chem.*, 38:4191–4197 (1995)). Ketoconazole, an active imidazole fungicide, has been used to reduce testosterone biosynthesis in the treatment of patients with advanced prostatic cancer (Trachtenberg, *J. Urol.*, 132:61–63 (1984); and Williams et al, *Br. J. Urol.*, 58:45–51 (1986)). However, ketoconazole is not very potent. Moreover, it has a number of significant side-effects, including inhibition of several other cytochrome $P_{450}$ steroidogenic enzymes, and reduction of cortisol production. Another drug used for prostate cancer, aminoglutethimide (AG), has similar drawbacks. This suggest that more potent and selective inhibitors of $P450_{17\alpha}$ could provide useful agents in treating this disease. In addition such compounds may be effective in treating breast cancer patients. AG was used for this purpose, but was associated with adverse side-effects.

In the prostate, 5α-reductase is the enzyme that converts testosterone to the more potent androgen, DHT, which stimulates prostatic growth. This enzyme occurs in two important isoforms, the Type I isoform expressed in human non-genital skin, and the Type II isoform present in the human prostate (Russell et al, *Ann. Rev. Biochem.*, 63:25–61 (1994)). The 5α-reductase inhibitor, N-[1,1-dimethyl-3-oxo-4-aza-5αandrost-1-ene-17β-carboxamide (finasteride; Merck) recently approved for treatment of BPH (Stoner, *J. Steroid Biochem. Molec. Biol.*, 37:375–378 (1990)) is a more potent inhibitor of the Type II than of the Type I isoform. However, finasteride is effective mainly in BPH patients with minimal disease, possibly because serum DHT levels have been found to be incompletely reduced (65–80%). As the Type I isoenzyme is probably the source of much of the residual plasma DHT, compounds that inhibit Type I as well as Type II may be more effective in patients.

More recently, another azasteroid, MK-434, has been described which reduces prostatic DHT levels in dogs more effectively than finasteride (Cohen et al, *The Prostate*, 26:55–71 (1995)). The main advantage of this compound, which has similar activity to finasteride in vitro, appears to be its more favorable pharmacokinetics. However, its efficacy in humans remains to be seen. Although finasteride and MK-434 reduce DHT levels, they also increase serum testosterone levels (Geller et al, *J. Clin. Endocrinol. Metab.*, 71:1552–1555 (1990). Preservation of testosterone levels may be an advantage in patients with BPH. However, inhibitors of 5α-reductase which increase testosterone levels may not be sufficiently effective in treating prostatic cancer since testosterone will bind to the AR in the absence of DHT. That is, while DHT binds to the AR with higher affinity than testosterone and dissociates more slowly, testosterone can bind to the AR when DHT levels are reduced (Gormley, *Urol. Clinics of North America*, 18(1):93–97 (1991)). As indicated above, despite significant reductions in prostatic DHT levels during treatment (Cohen et al, supra), these compounds are not as effective as castration. More importantly, it appears that they are less effective in eliciting prostatic cell death. The androgen-responsive gene, TRPM-2 associated with apoptosis is significantly enhanced by castration but, not by finasteride treatment (Rittinaster et al, *Mol. Endocrin.*, 5:1023–1029 (1991); and Shao et al *J. Androl.*, 14:79–86 (1993)). This has been attributed to the lower androgen levels after castration (Shao et al, supra), which is mainly a consequence of the reduction in testosterone production. Recent studies of patients receiving long-term treatment with finasteride found some patients developed gynecomastia which led to breast cancer in a few cases (Green et al, *Letter to New Eng. J. Med.*, 335(11):823-C (1996)). This raises concerns about the use of 5α-reductase inhibitors, since blockade of this step increases the conversion of androgen substrates to estrogens. Compounds which reduce production of testosterone and DHT as well as other androgens by inhibiting $P450_{17\alpha}$ would not be associated with this problem, and may be more effective in the treatment of prostatic cancer.

Several compounds which inhibit both $P450_{17\alpha}$ and 5α-reductase have been identified (Li et al, *J. Steroid Biochem. Mol. Biol.*, 42:313–321 (1992); Li et al, *The Prostate*, 26:140–150 (1995); and Li et al, *J. Med. Chem.*, 39:4335–5339 (1996)). Such compounds could block all androgen synthesis, i.e., testosterone, DHT and androstenedione, and be more effective alternatives or additions to orchiectomy in treating prostate cancer patients.

In pending U.S. patent application Ser. No. 08/795,932, filed Feb. 5, 1997; which is incorporated by reference herein in its entirety, compounds which inhibit androgen synthesis have been identified and purified.

In the present invention, additional compounds which inhibit androgen synthesis have been identified and purified. These compounds strongly inhibit $P450_{17\alpha}$, and are based on the finding that an imidazole moiety acts as a ligand to bind the iron atom of the heme prosthetic group of $P450_{17\alpha}$, and form a coordinated complex. Such compounds are potent inhibitors of aromatase, e.g., fadrozole, which is useful in the treatment of breast cancer (Lang et al, *J. Steroid Biochem. Molec. Biol.*, 44:421–428 (1993)). Although the detailed mechanism of the 17α-hydroxylation and $C_{17,20}$-side-chain cleavage by $P450_{17\alpha}$ in presently unclear, it appears that the $C_{17}$ and $C_{20}$ positions of the substrate must be close to the heme group of the enzyme. Thus, introduction of an imidazole group or other heterocyclic group with a nitrogen lone pair of electrons at these positions might coordinate to the iron atom of the prosthetic group in the active site of the enzyme (Green et al, supra). Using this rationale, a series of androstene derivatives (substrate-like compounds) with imidazole, pyrazole and oxazole groups substituted at the 17-position were synthesized in the present invention.

The compounds of the present invention, wherein the azole group is attached to the steroid nucleus via a nitrogen of the azole constitute a class of compounds not hitherto reported, and distinguish the compounds of the present invention from the known 17-azole androstene steriods.

SUMMARY OF THE INVENTION

An object of the present invention is to provide inhibitors of androgen biosynthesis.

Another object of the present invention is to provide a method for the synthesis of said inhibitors.

Still another object of the present invention is to provide pharmaceutical compositions containing the same.

Yet another object of the present invention is to provide methods for inhibiting synthesis of testosterone and/or DHT.

An additional object of the present invention is to provide methods for treatment of prostatic cancer and BPH.

These and other objects of the present invention, which will be apparent from the detailed description of the invention provided hereinafter, have been met, in one embodiment, by a compound of general Formula (I) or a pharmaceutically acceptable salt thereof:

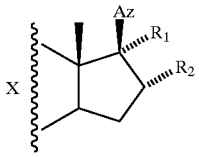

(I)

wherein X represents the residue of the A, B and C rings of a steroid consisting of a 4-en-3-one or 5-en-3β-ol system;

wherein Az represents an azole group attached to C-17 of the steroid via a hetero nitrogen atom; and wherein $R_1$ and $R_2$ each represents a hydrogen atom or together represent a double bond.

BRIEF DESCRIPTION OF THE DRAWINGS

FIG. 2A shows a Lineweaver-Burk analysis (1/v vs. i/[s]) of $\Delta^{16}$-17-(1H-imidazole) (Compound 11) at 3.0, 6.0 and 10 nM; while

DETAILED DESCRIPTION OF THE INVENTION

Figure 1A:
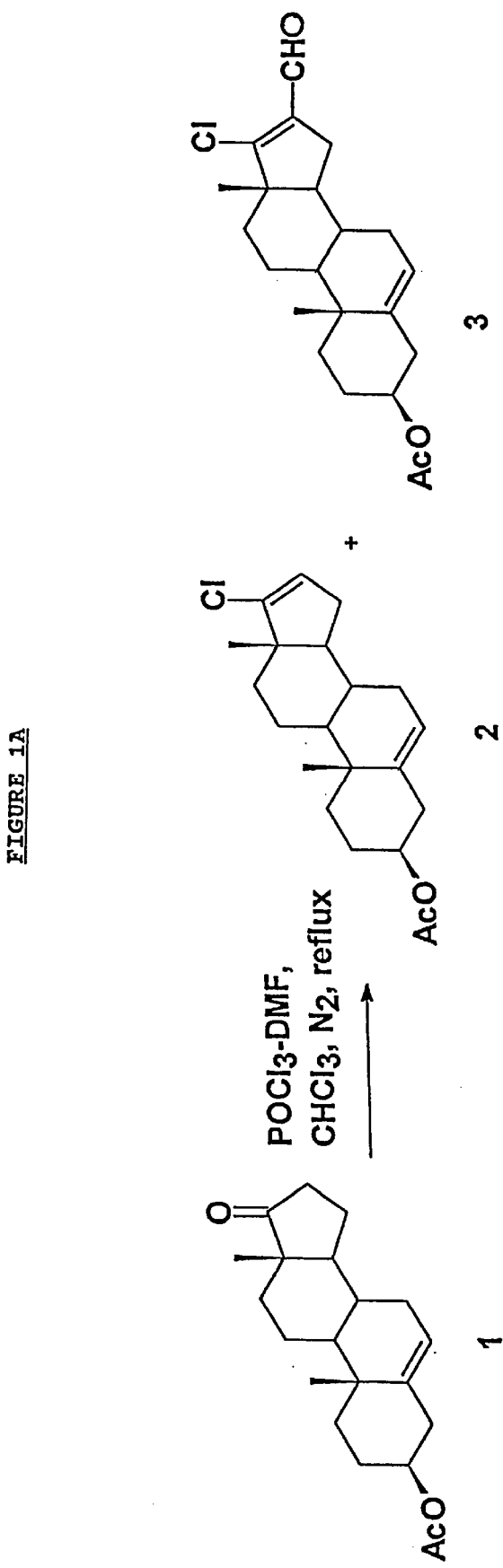
FIGS. 1A–1F show the schematic synthesis of Compounds 1–30 described in Synthesis Examples 1–25.
Figure 1B:
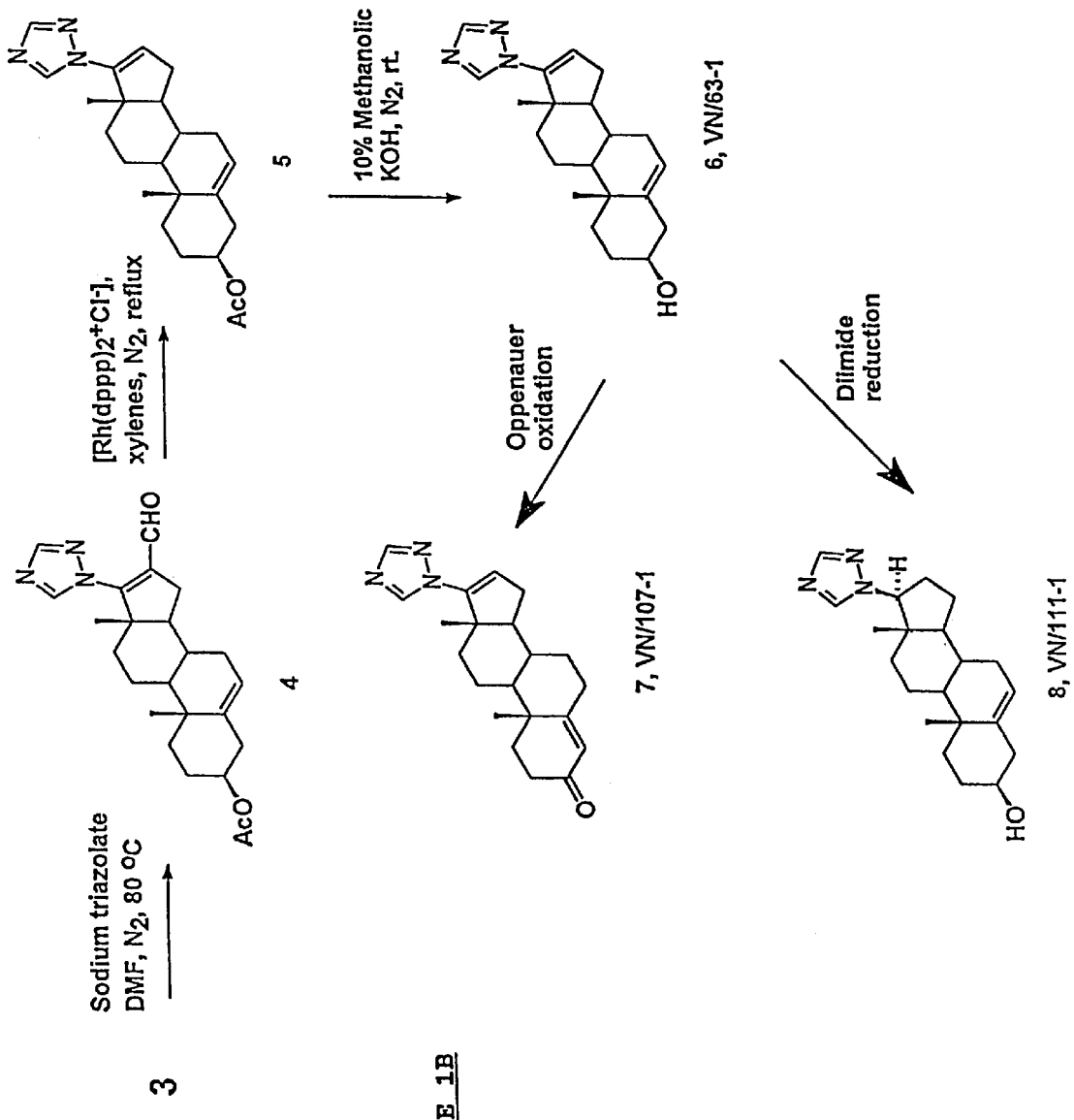
Figure 1C:
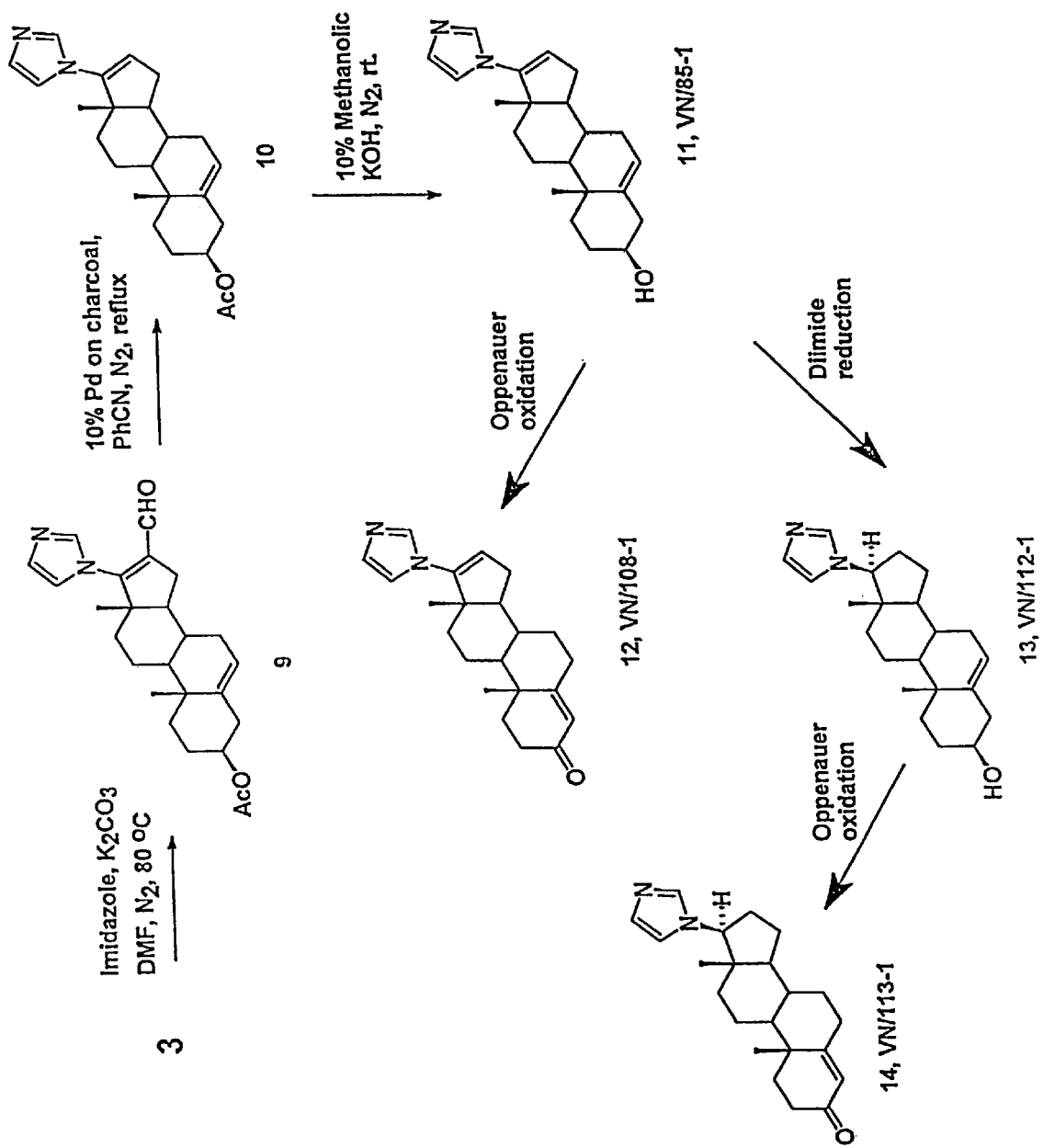
Figure 1D:
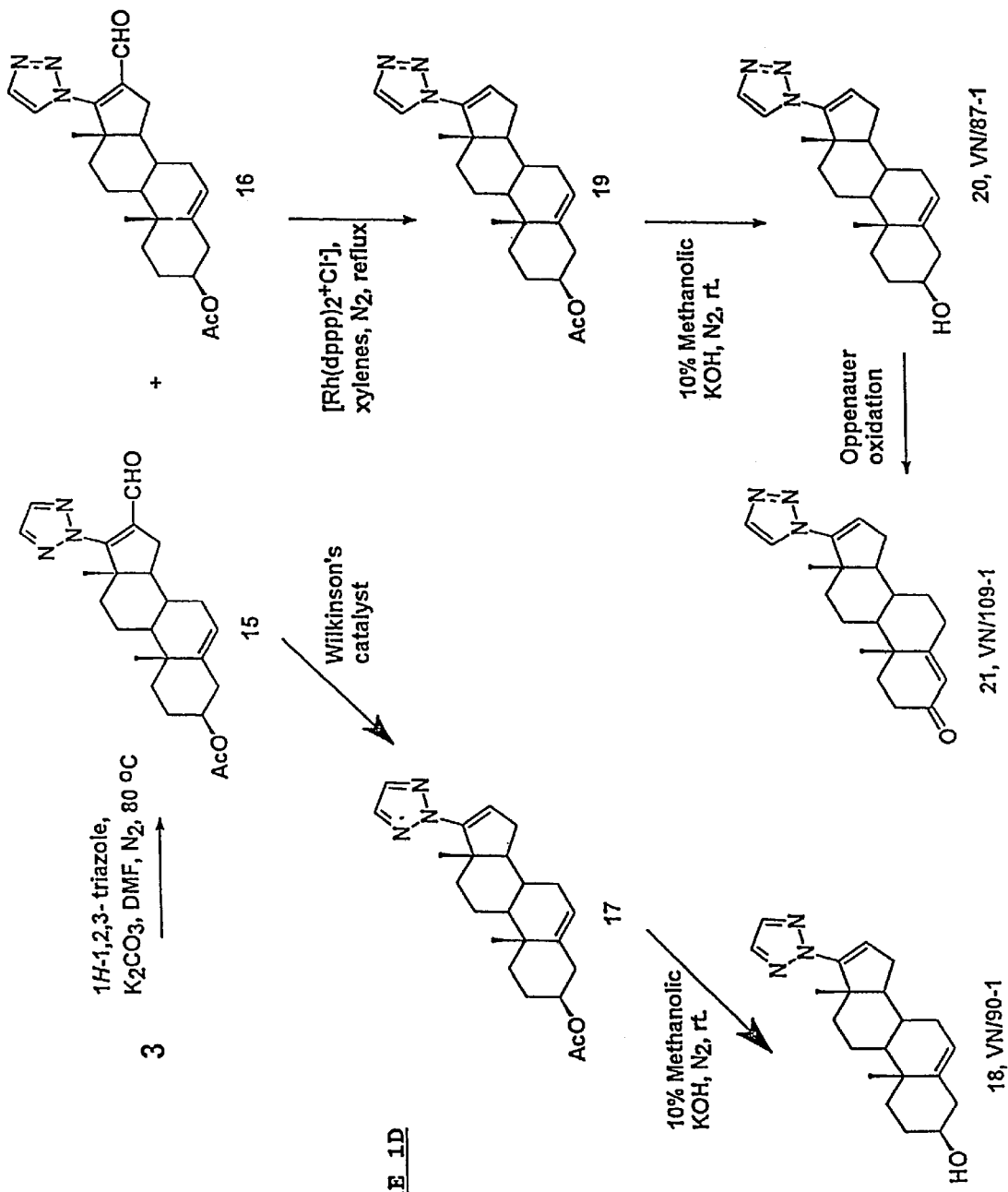
Figure 1E:
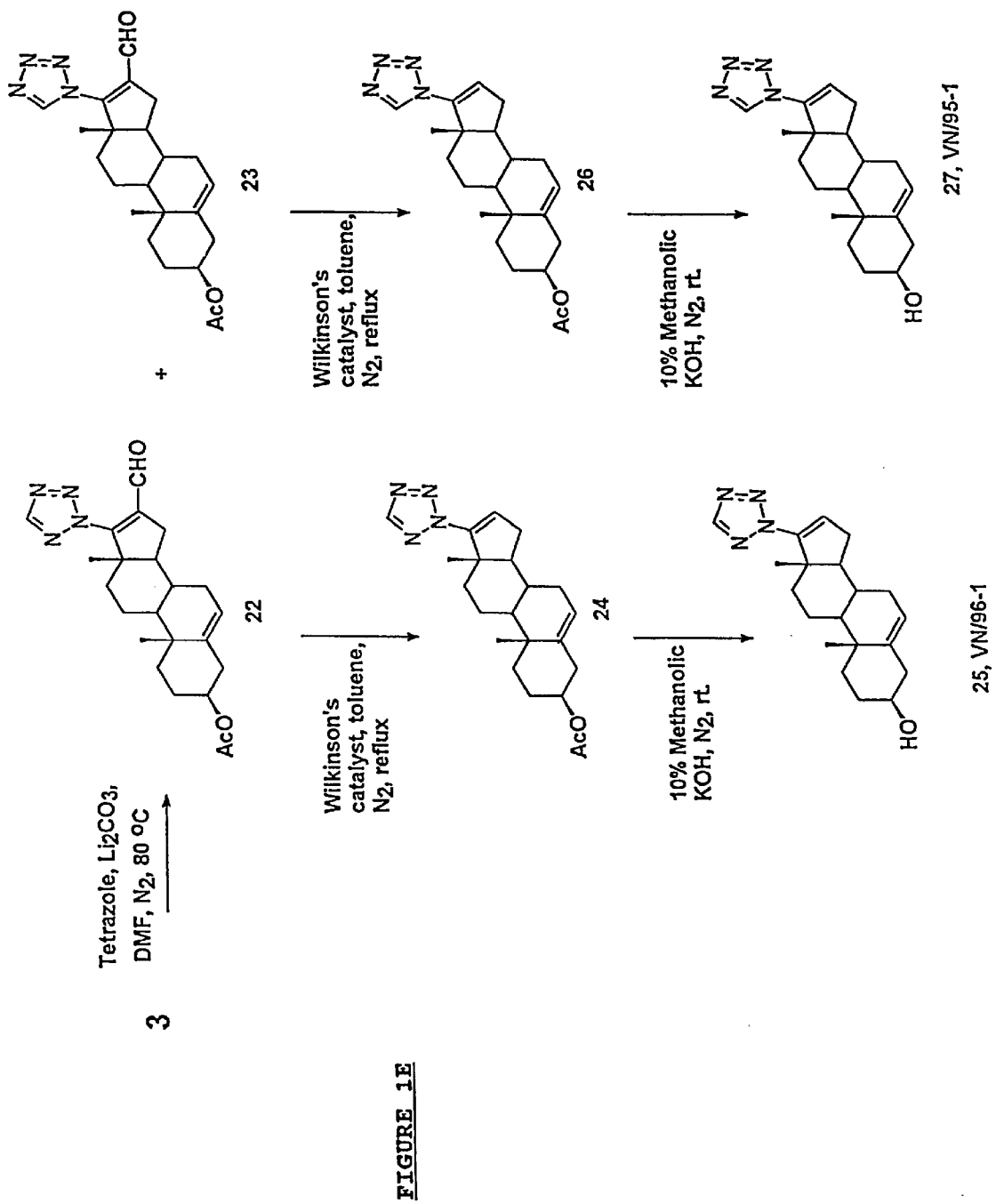
Figure 1F:
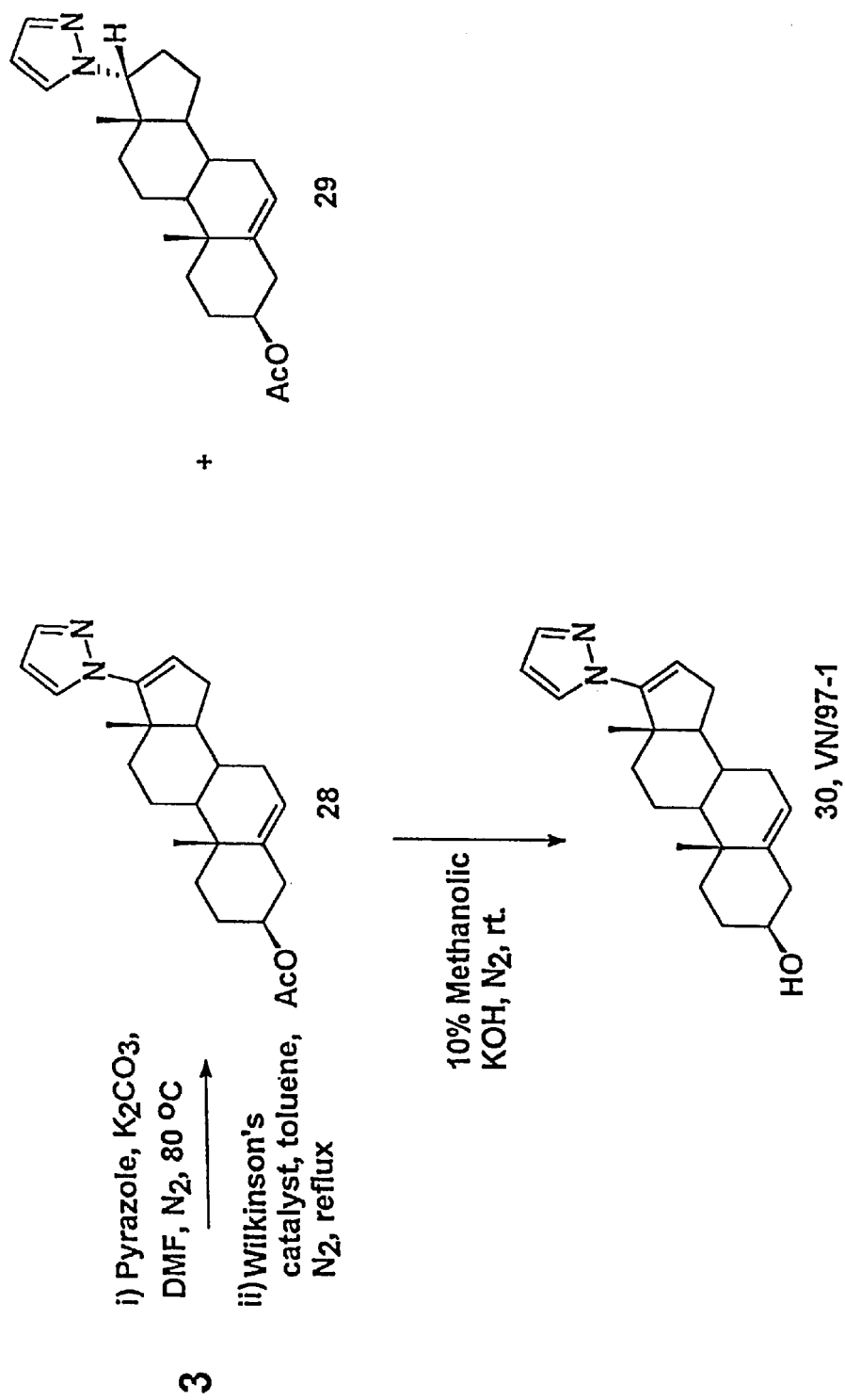

As discussed above, in one embodiment, the above-described object of the present invention have been met by a compound of general Formula (I) or a pharmaceutically acceptable salt thereof.

In Formula (I), X represents the residue of the A, B and C rings of a steroid consisting of 4-en-3-one or 5-en-3β-ol systems; Az represents an azole group attached to C-17 of the steroid via a hetero nitrogen atom; and $R_1$ and $R_2$ each represents a hydrogen atom or together represent a double bond.

Preferred examples of Az include the following groups

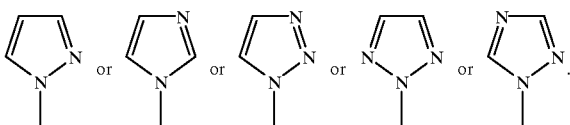

The steroid of Formula (I) preferably comprises a basic structure selected from the group consisting of $\Delta^4$-3-one, $\Delta^5$-3β-ol and $\Delta^{1,4}$-3-one.

Furthermore, the steroid is preferably an aza steroid comprising a ring nitrogen atom in place of a ring carbon atom, preferably the ring nitrogen is in the A ring, e.g., a 4-azasteroid; or the ring nitrogen is in the B ring, e.g., 6-azasteroid.

Specific examples of the compound of the present invention include the following compounds: 17-(1H-imidazolyl)-androst-5-en-3β-ol, 17β-(1H-imidazolyl)-androsta-5,16-dien-3β-ol, 17β-(1H-1,2,3-triazolyl)-androst-5-en-3β-ol, 17-(1H-1, 2,3-triazolyl) -androsta-5, 16-dien-3β-ol, 17β-(1H-1,2,4-triazolyl)-androst-5-en-3β-ol, 17-(1H-1, 2,4-triazolyl) -androsta-5,16-dien-3β-ol or 3-acetates thereof; and the following compounds: 17β-(1H-imidazolyl)-androst-4-en-3-one, 17-(1H-imidazolyl)-androsta-4,16-dien-3-one, 17β-(1H-1,2,3-triazolyl)-androst-4-en-3-one, 17-(1H-1, 2, 3-triazolyl) -androsta-4,16-dien-3-one, 17β-(1H-1,2,4-triazolyl)-androst-4-en-3-one, 17-(1H-1,2,4-triazolyl)-androsta-4,16-dien-3-one or 3-oximes thereof.

Acetates can be prepared as described in the Synthesis Examples provided herein.

Oximes can be prepared by refluxing the steroids with hydroxylamine hydrochloride in ethanol for 4 hrs, as adding water, and separating the crude mixture flash chromatography on silica gel.

The particular pharmaceutical acceptable salt of the compounds of the present invention is not critical thereto.

Examples of pharmaceutically acceptable base salts which can be used in the present invention include base salts derived from an appropriate base, such as alkali metal (e.g., sodium), alkaline earth metal (e.g., magnesium), ammonium, and $NW_nH_m$ bases, wherein each of n and m are 0 to 4 and n+m is 4, and wherein W is a $C_1$–$C_{18}$ alkyl.

Examples of pharmaceutically acceptable salts of an acid group which can be employed in the present invention include salts of organic carboxylic acids, such as acetic, citric, oxalic, lactic, tartaric, malic, isothionic, lactobionic, ascorbic and succinic acids; organic sulfonic acids, such as methanesulfonic, ethanesulfonic, benzenesulfonic and p-tolylsulfonic acids; and inorganic acids, such as hydrochloric, sulfuric, phosphoric, hydrobromic and sulfamic acids.

The pharmaceutically acceptable salt may be also a salt of an amino group, or a 3-hydroxy ester.

Examples of pharmaceutically acceptable salts of an amino group include salts of the inorganic or strong organic acids noted above.

Examples of pharmaceutically acceptable salts of a hydroxy group include the anion of the compound in to combination with a suitable cation, such as $Na^+$, and $NW_nH_m$, wherein W is a $C_1$–$C_{18}$ alkyl group, and n and m are 0 to 4, and n+m is 4.

The compounds of Formula (I) can be prepared by a methodology starting from the 3β-acetoxyandrost-5-en-17- one represented by Formula (II) (which is commercially available from Aldrich, Milwaukee, Wis.):

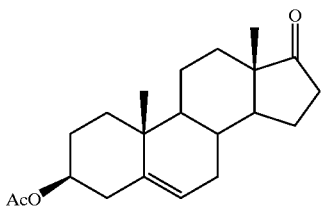

(II)

This method involves conversion of the compound represented by Formula (II) following the Vilsmeier-Haack reaction (Siddiqui et al, *J. Heterocyclic Chem.*, 32:353–354 (1995)) with phosphorous oxychloride ($POCl_3$) and dimethylformamide (DMF) to give the 3β-acetoxy-17-chloro-16-formylandrosta-5,16-diene represented by Formula (III):

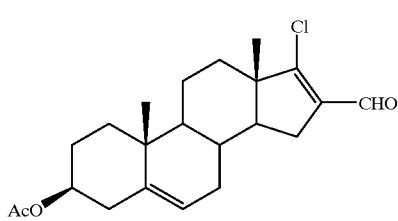

(III)

Treatment of the compound represented by Formula (III) with a variety of azole nucleophiles in (DMF) at 75–80° C. under $N_2$ atmosphere gives high yields (73–92%) of the 17-azole-$\Delta^{16}$ steroids represented by Formula (IV):

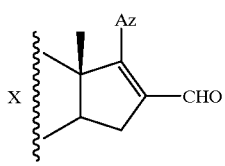

(IV)

wherein X represents A, B and C rings. Of the compound represented by Formula (III).

Following decarbonylation at C-16 and cleavage of the 3β-acetoxy group, the 5-en-3β-ol-17-azole compounds of Formula (V) are obtained; while oppenauer oxidation of these compounds yields their corresponding 4-en-3-one-17-azole counterparts.

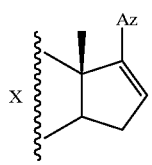

(V)

wherein X is as defined for the compounds of Formula (I).

Analogues of a saturated D-ring can be prepared from the corresponding $\Delta^{16}$ compounds by reduction with diimide (Potter et al, supra).

A mechanism for the formation of the compound represented by Formula (IV) is outlined in the following reaction scheme; a nucleophilic vinylic "addition-elimination" substitution reaction. Recent studies in this field favor path a of the Reaction Scheme (Rappoport, *Acc. Chem. Res.*, 25:474–480 (1992)).

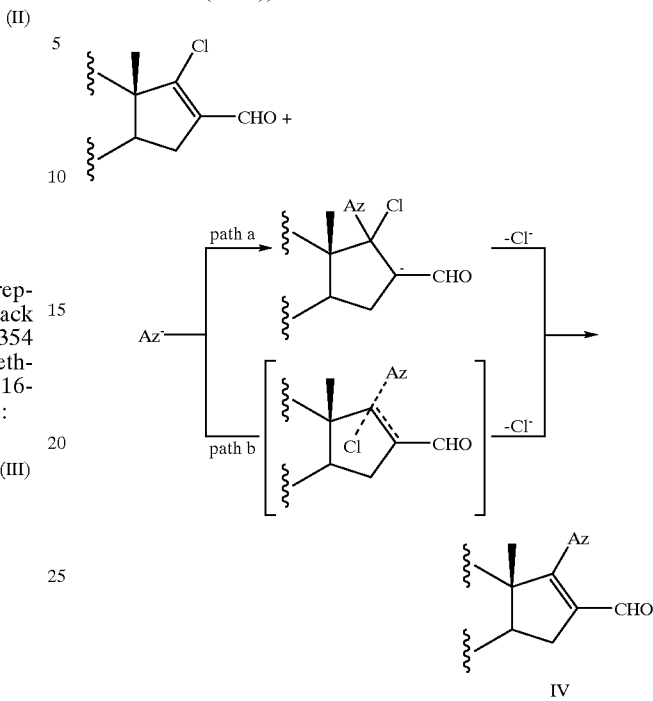

It has been found in the present invention that the azoles represented by Formula (I) are potent inhibitors of 17α-hydroxylase-$C_{17,20}$-Lyase (hereafter referred to as "$P450_{17\alpha}$"), the enzyme which catalyzes the conversion of progesterone and pregnenolone into the androgens, androstenedione and dehydroepiandrosterone, respectively. Since androgens are implicated in the etiology of a number of androgen-dependent diseases, e.g., prostate cancer, inhibitors of $P450_{17\alpha}$ are useful for the treatment of these diseases. In addition, in has been found in the present invention that some of these potent $P450_{17\alpha}$ inhibitors are also potent inhibitors of 5α-reductase, while some have strong anti-androgen activity. Because of their dual activities, the compounds of the present invention are believed to be more effective than the current agents in the treatment of prostate cancer and other disease states which depend upon androgens.

Thus, as discussed above, in still another embodiment, the above-described objects of the present invention have been met by a pharmaceutical composition for reducing plasma levels of testosterone and/or DHT in a mammal in need of such treatment comprising:

(A) a pharmaceutically effective amount of at least one compound of Formula (I) or a pharmaceutically acceptable salt thereof, and (B) a pharmaceutically acceptable carrier or diluent.

The compound may be present in the composition in amount of 0.01 to 99.9 wt %, and more preferably in about 0.1 to 99 wt % of the composition. Still more preferably, the compound may be present in the composition in an amount of about 1.0 to 70 wt % of the composition.

The particular carrier or diluent employed is not critical to the present invention. Typically, the carrier or diluent may be a solid, liquid, or vaporizable carrier, or combinations thereof. Examples of such carriers or diluents include water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters, such as sodium chloride, glucose or glycerin can be added to make the preparations isotonic. Aqueous sterile injection solutions may further contain anti-oxidants, buffers, bacteriostats, and like additives acceptable for parenteral formulations.

In addition, the pharmaceutical composition can contain excipients, such as fillers, binders, wetting agents, disintegrators, surface-active agents, lubricants, and the like.

The pharmaceutical composition can be prepared in accordance with accepted pharmaceutical procedures, for example, as described in *Remington's Pharmaceutical Sciences,* Seventeenth Edition, ed. Gennaro, Mack Publishing Company, Easton, Pa. (1985).

The composition may be in a unit dosage form. Typical unit dosage forms include tablets, pills, powders, solutions, suspensions, emulsions, granules, capsules, suppositories, injectable solutions and suspensions.

As discussed above, in yet another embodiment, the above-described objects of the present invention have been met by a method of inhibiting synthesis, i.e., plasma levels, of testosterone and/or DHT comprising administering to a subject in need of such treatment, a pharmaceutically effective amount of at least one compound of Formula (I) or a pharmaceutically acceptable salt thereof.

The mode of administering is not critical to the present invention. Examples of the mode of administering include oral, rectal, nasal, topical (including buccal and sublingual), and parenteral (including subcutaneous, intramuscular, intravenous, intradermal, and transdermal) administration. The preferred modes of administration are oral, nasal, topical and parenteral administration.

The amount of compound of Formula (I) to be administered varies depending upon the age, weight and species of the subject, the general health of the subject, the severity of the symptoms, whether the composition is being administered alone or in combination with other therapeutic agents, the incidence of side-effects and the like.

In general, a dose suitable for treatment of BPH is about 0.001 to 100 mg/kg body weight/dose, preferably about 0.01 to 60 mg/kg body weight/dose, and still more preferably about 0.1 to 40 mg/kg body weight/dose per day. A dose suitable treatment of prostate cancer is about 0.001 to 100 mg/kg body weight/dose, preferably about 0.01 to 60 mg/kg body weight/dose, and still more preferably about 0.1 to 40 mg/kg body weight/dose per day. The desired dose may be administered as 1 to 6 or more subdoses administered at appropriate intervals throughout the day. The compounds may be administered repeatedly over a period of months or years, or may be slowly and constantly infused to the subject. Higher and lower doses may also be administered.

The daily dose may be adjusted taking into account, for example, the above-identified variety of parameters. Typically, the compounds of Formula (I) may be administered in an amount of about 0.001 to 100 mg/kg body weight/day. However, other amounts may also be administered.

To achieve good plasma concentrations, the compounds may be administered, for instance, by intravenous injection of an approximate 0.1 to 1.0% (w/v) solution of the active ingredient, optionally in saline, or orally administered as a bolus.

In yet another embodiment, the above-described objects of the present invention have been met by a method of treating BPH or prostate cancer, or inhibiting the growth of prostate tissue, in a subject in need of such treatment comprising administering a pharmaceutically effective amount of the compound of Formula (I) or a pharmaceutically acceptable salt thereof.

The above-described methods may be practiced by administration of the compounds by themselves or in a combination with other active ingredients, including other steroid compounds and/or therapeutic agents. Other therapeutic agents suitable for use herein are any compatible drugs that are effective by the same or other mechanisms for the intended purpose, or drugs that are complementary to those of the present agents. These compounds include agents that are effective for the inhibition of testosterone and/or DHT synthesis, and in the treatment of prostate cancer, anticancer agents. Examples of such compounds include ketoconazole, finasteride, and 4MA.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained.

The following examples are provided for illustrative purposes only, and are in no way intended to limit the scope of the present invention.

In the Synthesis Examples (see FIGS. 1A–1F), $^1$H NMR data (300 MHZ) (internal standard Me$_4$Si=δ0) were recorded on a QE 300, NMR system, General Electric Co., in CDCl$_3$ unless otherwise stated.

Synthesis reactions were monitored by TLC on silica gel plates (Merck Type 60H), and visualized by dipping in 4.0% (v/v) sulfuric acid in ethanol followed by heating at about 120–150° C.

Flash column chromatography was carried out on silica gel (Merck grade 9385, 230–400 mesh 60 Å) in the solvent systems indicated.

LP refers to petroleum fractions, b.p. 35–60° C.

Solutions were dried using anhydrous Na$_2$SO$_4$.

Melting points were measured on a Fischer-Johns Melting Point apparatus and are uncorrected.

Synthesis Example 1

This Example describes a Vilsmeier-Haack reaction of 3β-acetoxyandrost-5-en-17-one (Compound 1), 3β-acetoxy-17-chloroandrosta-5,16-diene (Compound 2) and 3β-acetoxy-17-chloro-16-formylandrosta-5,16-diene (Compound 3).

A solution of 3β-acetoxyandrost-5-en-17-one (Compound 1) (2.0 g, 6.6 mmol) in dry chloroform (40 ml) was added dropwise to a cold and stirred solution of POCl$_3$ (10 ml) and DMF (10 ml). The mixture was allowed to attain room temperature, and then ref luxed under N$_2$ for 5 h. It was then concentrated under reduced pressure, and poured onto ice followed by extraction with a mixture of ether and EtOAc (8:2 (v/v)). The combined extracts were washed with brine, dried (Na$_2$SO$_4$), and solvent removed to give a white solid (2.3 g). Analytical TLC (silica gel, pet. ether/EtOAc, (10:1)) revealed the presence of two compounds, both less polar than (Compound 1). Purification by flash column chromatography (FCC, silica gel, pet. ether/EtOAc, (15:1)) gave Compound 2 (0.24 g, 11.4%) and Compound 3 (1.75 g, 77%).

Analytical and spectroscopic data for Compound 2 and Compound 3 were as follows:

Compound 2: m.p. 160–162° C.; $^1$H NMR (300 MHz, CDCl$_3$): δ 0.89 (3H, s, 18-Me), 1.06 (3H, s, 19-Me), 2.04

(3H, s, 3β-OAc), 4.61 (1H, m, 3α-H), 5.39 (1H, d, J=4.8 Hz, 6-H) and 5.63 (1H, d, J=0.9 Hz, 16-H). Analysis calculated for $C_2H_2O_2Cl$: C, 72.38; H, 8.39. Found: C, 72.72; H, 8.60. HRMS calcd. for $C_{21}H_{29}O_2Cl$, 348.1856, found 348.1766.

Compound 3: m.p. 163–165° C.; $^1H$ NMR (300 MHz, $CDCl_3$): δ 0.99 (3H, s, 18-Me), 1.07 (3H, s, 19-Me), 2.04 (3H, s, 3β-OAc), 4.60 (1H, m, 3a-H), 5.40 (1H, d, J=4.8 Hz, 6-H) and 9.99 (1H, s, 16-CHO). Analysis calculated for $C_2H_2O_3Cl$: C, 70.11; H, 7.76. Found: C, 70.18; H, 7.82. HRMS calcd. for $C_{21}H_{29}O_3Cl$, 376.1805, found 376.1748.

Synthesis Example 2

This Example describes the preparation of 3β-acetoxy-17-(1H, 1,2,4-triazol-1-yl)-16-formylandrosta-5,16-diene (Compound 4).

A solution of 3β-acetoxy-17-chloro-16-formylandrosta-5, 16-diene (Compound 3) (0.6 g, 1.6 mmol) and sodium triazolate (436 mg, 4.79 mmol, 3 equiv.) in dry DMF (10 ml) under $N_2$ was stirred at 78° C. for 30 min. After cooling to room temperature, the reaction mixture was poured onto ice-water (250 ml), and the resulting white precipitate was filtered, washed with water, and dried to give a white solid. This was crystallized from hexane/EtoAc to give Compound 4 (580 mg, 89%), m.p. 160–162° C. $^1H$ NMR (300 MHz, $CDCl_3$): δ 1.08 (3H, s, 18-Me), 1.20 (3H, s, 19-Me), 2.04 (3β, s, 30-OAc), 4.61 (1H, m, 3a-H), 5.42 (1H, d, J=4.2 Hz, 6-H), 8.13 (1H, s, 3α-H), 8.42 (1H, s, 5'-H) and 10.12 (1H, s, 16-CHO). Analysis calculated for $C_{24}H_{31}O_3N_3$: C, 70.37; H, 7.63; N, 10.27 Found: C, 70.28; H, 7.82; N, 10.21. HRMS calcd. for $C_4H_{31}O_3N_3$ 409.2365, found 409.2348.

Synthesis Example 3

This Example described the preparation of 3β-acetoxy-17-(1H,1,2,4-triazol-1-yl)androsta-5,16-diene (Compound 5) by either method (1) or method (2). the latter method gives a better yield of Compound 5.

Method (1):

A mixture of the 17-triazole-16-formyl (Compound 4) (450 mg, 1.22 mmol) in dry toluene (15 ml) and Wilkinson's catalyst (1.04 g, 1.253 mmol, 1.025 equiv.) was refluxed under $N_2$ for 2 h. The reaction mixture was concentrated to give a brown residue. This was treated with $CH_2Cl_2$ (saturated with $NH_3$), and the resulting yellow by-product was filtered; the filtrate concentrated to give a light yellow solid (375 mg) which was subjected to chromatography over silica gel. Elution with $CH_2Cl_2$ (saturated with $NH_3$) afforded Compound 5 (300 mg, 72%); m.p. 187–190° C. (from hexane/EtOAc). $^1H$ NMR (300 MHz, $CDCl_3$): δ 1.08 (3H, s, 18-Me), 1.10 (3H, s, 19-Me), 2.04 (3H, s, 3β-OAc), 4.62 (1H, m, 3α-H), 5.42 (1H, d, J=4.5 Hz, 6-H), 5.96 (1H, s, 16-H), 7.99 (1H, s, 3'-H) and 8.26 (1H, s, 5'-H). Analysis calculated for $C_{23}H_{31}O_2N_3$: C, 72.40; H, 8.19; N, 11.02. Found: C, 72.30; H, 8.16; N, 11.00. HRMS calcd. for $C_{23}H_{31}O_2N_3$ 381.2416, found 381.2406.

Method (2):

A mixture of bis(triphenylphosphine)rhodium(1) carbonyl chloride (338 mg, 0.489 mmol) and 1, 3-bis(diphenylphosphino) propane (440 mg, 1.065 mmol) in dry xylenes (40 ml) was stirred at 80° C. under $N_2$ for 15 min when a fine yellow precipitate formed. 3β-Acetoxy-17-(1H-1,2,4-triazol-1-yl)-16-formylandrosta-5,16-diene (Compound 4), 2.0 g, 4.89 mmol) was added, and the mixture was refluxed under $N_2$ for 15 h; then cooled, and concentrated under reduced pressure. The crude product was dissolved in EtOAc (200 ml) and filtered through a 4.0 cm pad of silica gel (70–230 mesh). The silica was washed with EtOAc (2×200 ml), and the combined filtrates were evaporated to give the crude product. This was purified by FCC (silica gel, pet. ether/EtOAc/$Et_3N$, (7.7:2:0.3)) to give Compound 5 (1.63 g, 87.6%). Spectroscopic and analytical data were the same as given in Method 1 above.

Synthesis Example 4

This Example describes the preparation of 3β-hydroxy-17-(1H, 1,2,4-triazol-1-yl)androsta-5,16-diene (Compound 6), VN/63-1.

The acetate of Compound 5 (150 mg) in dry methanol (2.0 ml) under $N_2$ was treated with 10% methanolic KOH (1.0 ml). The mixture was stirred at room temperature for 1 h, and then concentrated under reduced pressure to a volume of about 1.0 ml. It was diluted with ice-cold water (20 ml), the resulting precipitate was washed ($H_2O$), dried to give Compound 6 (120 mg, 90%); m.p. 185–189° C. (decomp.). $^1H$ NMR (300 MHz, $CDCl_3$): δ 1.07 (3H, s, 18-Me), 1.10 (3H, s, 19-Me), 3.55 (1H, m, 3a-H), 5.39 (1H, d, J=4.8 Hz, 6-H), 5.96 (1H, s, 16-H), 7.99 (1H, s, 3'-H) and 8.26 (1H, s, 51-H). Analysis calculated for $C_{21}H_{29}ON_3$: C, 74.29; H, 8.83; N, 12.38. Found: C, 74.20; H, 8.63; N, 12.34. HRMS calcd. for $C_{21}H_{29}ON_3$ 339.2311, found 339.2297.

Synthesis Example 5

This Example describes the preparation of 17-(1H, 1,2,4-triazol-1-yl)androsta-4,16-diene-3-one (Compound 7), VN/107-1.

From a mixture of 3β-hydroxy-17-(1H-1,2,4-triazol-1-yl)-androsta-5,16-diene (Compound 6) (250 mg, 0.7381 mmol), 1-methyl-4-piperidone (1.18 ml) and toluene (20 ml) was distilled off about 4.0 ml. Aluminum isopropoxide (253 mg 1.241 mmol) was then added and the mixture was refluxed under $N_2$ for 4 h. After cooling, the mixture was diluted with EtOAc (30 ml), washed successively with 5.0% aq. $NaHCO_3$ (×3) and brine (×2), and then dried ($Na_2SO_4$). The solvent was evaporated and the crude product was purified by FCC (silica gel, $CH_2Cl_2$/EtOH, (30:1)) to give Compound 7 (200 mg, 80.5%), mp 247–250° C. $^1H$ NMR (300 MHz, $CDCl_3$): δ 1.13 (3H, s, 18-Me), 1.24 (3H, s, 19-Me), 5.76 (1H, s, 16-H), 5.95 (1H, s, 4-H), 8.00 (1H, s, 3'-H), and 8.26 (1H, s, 5'-H). Analysis calculated for $C_{21}H_{27}ON_3$:C, 74.73; H, 8.07; N, 12.46. Found: C, 74.54; H, 8.00; N, 12.50.

Synthesis Example 6

This Example describes the preparation of 3β-hydroxy-17β-(1H-1,2,4-triazol-1-yl)androst-5-ene (Compound 8), VN/111-1.

A mixture of Compound 6 (200 mg, 0.590 mmol), hydrazine hydrate (0.57 ml, 1.77 mmol), and acetic acid (0.35 ml) in EtOH (20 ml) was heated at 80° C. while a stream of air was passed through the solution for 6 h. The reaction mixture was concentrated to about 10 ml and after cooling, it was diluted with EtOAc (30 ml) followed by washing with saturated aqueous $NaHCO_3$ (10 ml×2), and brine (10 ml×2), dried ($Na_2SO_4$) and concentrated to give a crude product (190 mg). This was purified by FCC (silica gel, $CH_2Cl_2$/EtOH, (30:1)) to give the Compound 8 (150 mg, 10–74.6%), mp 246–248° C. $^1H$ NMR (300 MHz, $CDCl_3$): δ 0.56 (3H, s, 18-Me), 1.01 (3H, s, 19-Me), 3.53 (1H, m, 3α-H), 4.19 (1H, t, J 9.6 Hz, 17a-H), 5.37 (1H, d, J=5.2 Hz, 6-H), 7.93 (1H, s, 3'-H) and 8.10 (1H, s, 5'-H). Analysis calculated for $C_{21}H_{31}ON_3$: C, 73.85; H, 9.16; N, 12.31. Found: C, 73.75; H, 9.40; N, 12.28.

Synthesis Example 7

This Example describes the preparation of 3β-acetoxy-17-(1H-imidazol-1-yl) -16-formylandrosta-5, 16-diene (Compound 9).

A mixture of 3β-acetoxy-17-chloro-16-formylandrosta-5, 16-diene (Compound 3) (500 mg, 1.329 mmol), imidazole (136 mg, 2.0 mmol) and $K_2CO_3$ (551 mg, 3.99 mmol) in dry DMF was heated at about 80° C. under $N_2$ for 2 h. After cooling to room temperature, the reaction mixture was poured onto ice-cold water (100 ml), and the resulting white precipitate was filtered, washed with water, and dried to give a white solid. This was titrated with boiling mixture of hexane/EtOAc to give Compound 9 (520 mg, 92%), mp 218–220° C. $^1$H NMR (300 MHz, $CDCl_3$): δ 1.08 (6H, s, 18 and 19-Me), 2.04 (3H, s, 3f-OAc), 4.61 (1H, m, 3α-H), 5.42 (1H, d, J=4.8 Hz, 6-H), 7.11 (1H, s, 4'-H), 7.23 (1H, s, 5'-H), 7.63 (1H, s, 2'-H) and 9.74 (1H, s, 16-CHO). Analysis calculated for $C_{25}H_{32}O_3N_2$: C, 73.49; H, 7.90; N, 6.88; Found: C, 73.34; H, 8.05; N, 6.65. HRMS calcd. for $C_{25}H_{32}O_3N_2$ 408.2413, found 408.2426.

Synthesis Example 8

This Example describes the preparation of 3β-acetoxy-17- (1H-imidazol-1-yl) androsta-5,16-diene (Compound 10).

A solution of 3β-acetoxy-17-(1H-imidazol-1-yl)-16-formylandrosta-5,16-diene (Compound 9) (4.0 g, 9.8 mmol) in dry benzonitrile (40 ml) was refluxed in the presence of 10% palladium on activated charcoal (2.0 g, i.e., 50% weight of the 16-formyl azole) for 3.5 h. After cooling to room temperature, the catalyst was removed by filtration through a Celite pad. The filtrate was evaporated and the residue was purified by FCC (silica gel, pet. ether/EtOAc/$Et_3N$, (6:4:0.3)) to give Compound 11 (2.72 g, 73.2%); mp 138–140° C. $^1$H NMR (300 MHz, $CDCl_3$): δ 1.0 (3H, s, 18-Me), 1.07 (3H, s, 19-Me), 2.04 (3H, s, 3f-OAc), 4.60 (1H, m, 3α-H), 5.41 (1H, s, 6-H), 5.68 (1H, s, 16-H), 7.02 (1H, s, 4'-H), 7.08 (1H, s, 5'-H), and 7.60 (1H, s, 2'-H). Analysis calculated for $C_{25}H_{32}O_3N_2$: C, 73.49; H, 7.90; N, 6.88; Found: C, 73.34; H, 8.05; N, 6.65. HRMS calcd. for $C_{25}H_{32}O_3N_2$ 408.2413, found 408.2426.

Synthesis Example 9

This Example describes the preparation of 3β-hydroxy-17- (1H-imidazol-1-yl) androsta-5,16-diene (Compound 11), VN/85-1.

The method followed that described in Synthesis Example 4, but using 3,6-acetoxy-17-(1H-imidazol-1-yl) -androsta-5,16-diene (Compound 10) (2.72 g, 7.16 mmol) in methanol (30 ml), 10% methanolic KOH (17 ml), and the mixture was stirred at room temp under $N_2$ for 2 h. Following the conventional workup gave rise to Compound 11 (2.34 g, 95%), mp 220–223° C. $^1$H NMR (300 MHz, $CDCl_3$): δ 1.01 (3H, s, 18-Me), 1.06 (3H, s, 19-Me), 3.53 (1H, m, 3α-H), 5.39 (1H, d, J=5 Hz, 6-H), 5.69 (1H, s, 16-H), 7.08 (2H, br. s, 4' and 5'-H), and 7.64 (1H, s, 2'-H). Analysis calculated for $C_{22}H_{30}ON_2$: C, 78.05; H, 8.94; N, 8.28; Found: C, 78.02; H, 9.00; N, 8.22. HRMS calcd. for $C_{22}H_{30}ON_2$ 338.2358, found 338.2361.

Synthesis Example 10

This Example describes the preparation of 17-(1H-imidazol-1-yl)androsta-4,16-diene-3-one (Compound 12), VN/108-1.

The method followed that described in Synthesis Example 5, but using 3,-hydroxy-17-(1H-imidazol-1-yl)-androsta-5, 16-diene (Compound 11) (200 mg, 0.59 mmol). Purification of the crude product by FCC (silica gel, $CH_2Cl_2$/EtOH, (40:1)) gave Compound 12 (150 mg, 75.4%), mp 147–150° C. $^1$H NMR (300 MHz, $CDCl_3$): δ 1.03 (3H, s, 18 -Me), 1.23 (3H, s, 19-Me), 5.69 (1H, s, 6-H), 5.76 (1H, s, 16- H), 7.10 (2H, br. s, 4' and 5'-H), and 7.63 (1H, s, 2'-H). Analysis calculated for $C_{22}H_{28}ON_2$: C, 78.52; H, 8.39; N, 8.33; Found: C, 78.30; H, 8.42; N, 8.23.

Synthesis Example 11

This Example describes the preparation of 3β-Hydroxy-17β-(1H-imidazol-1-yl)androst-5-ene (Compound 13), VN/112-1.

The method followed that described for Synthesis Example 6, but using 3β-hydroxy-17-(1H-imidazol-1-yl) androsta-5,16-diene (Compound 11) (170 mg, 0.505 mmol) and after purification by FCC (silica gel, $CH_2Cl_2$/EtOAc/ $Et_3N$, (7.7:2.0:0.3)) gave Compound 13 (110 mg, 64.3%), mp 255–258° C. $^1$H NMR (300 MHz, $CDCl_3$): δ 0.58 (3H, s, 18-Me), 1.01 (3H, s, 19-Me), 3.53 (1H, m, 3α-H), 3.98 (1H, t, J=9.8 Hz, 17α-H), 5.38 (1H, d, J=5.4 Hz, 6-H), 6.96 (1H, s, 4'-H), 7.04 (1H, s, 5'-H), and 7.54 (1H, s, 2'-H). Analysis calculated for $C_{22}H_{32}ON_2$: C, 77.59; H, 9.48; N, 8.23; Found: C, 77.55; H, 9.40; N, 8.31.

Synthesis Example 12

This Example describes the preparation of 17β-(1H-imidazol-1-yl)androst-4-ene-3-one (Compound 14), VN/113-1.

The method followed that described for Synthesis Example 5, but using 3β-Hydroxy-17β-(1H-imidazol-1-yl) androst-5-ene (Compound 13) (60 mg, 0.1765 mmol). Purification of the crude product by FCC (silica gel, $CH_2Cl_2$/ EtOH, (30:1)) gave Compound 12 (43 mg, 72%), mp 196–198° C. $^1$H NMR (300 MHz, $CDCl_3$): δ 0.61 (3H, s, 18-Me), 1.19 (3H, s, 19-Me), 3.97 (1H, t, J=9.6 Hz, 17α-H), 5.75 (1H, s, 6-H), 6.97 (1H, s, 4'-H)07 (2H, s, 5'-H), and 7.57 (1H, s, 2'-H). Analysis calculated for $C_{22}H_{30}ON_2$: C, 78.05; H, 8.94; N, 8.23; Found: C, 78.10; H, 8.90; N, 8.21.

Synthesis Example 13

This Example describes the reaction of 3β-acetoxy-17-chloro-16-formylandrosta-5, 16-diene (Compound 3) with 1H-1,2,3-Triazole and $K_2CO_3$ to give 3β-acetoxy-17-(2H-1,2,3-triazol-2-yl)-16-formylandrosta- 5,16-diene (Compound 15) and 3β-acetoxy-17- (1-H-1, 2, 3-triazol-1-yl) -16-formylandrosta-5, 16-diene (Compound 16), respectively.

A mixture of 3β-acetoxy-17-chloro-16-formylandrosta-5, 16-diene (Compound 3) (2.0 g, 5.23 mmol), 1H-1,2,3-triazole (552 mg, 7.98 mmol) and $K_2CO_3$ (2.20 g, 15.95 mmol) in dry DMF (40 ml) was heated at 80° C. under $N_2$ atmosphere for 2 h. After cooling to room temperature, the reaction mixture was poured onto ice-water (400 ml), and the resulting precipitate was filtered, washed with water, and dried to give a dirty white solid. This was subjected to flash chromatography, and on elution with pet. ether/EtOAc/$Et_3N$, (6.7:3:0.3), gave firstly 3β-acetoxy-17-(2H-1,2,3-triazol-2-yl)-16-formylandrosta-5,16-diene (Compound 15) (684 mg, 28%), mp 145–148° C. $^1$H NMR (300 MHz, $CDCl_3$): δ 1.09 (3H, s, 18-Me), 1.26 (3H, s, 19-Me), 2.04 (3H, s, 3β,-OAc), 4.61 (1H, m, 3α-H), 5.42 (1H, d, J=4.2 Hz, 6-H), 7.85 (2H, s, 4' and 5'-H) and 10.55 (1H, s, 16-CHO). Analysis calculated for $C_{24}H_{31}O_3N_3$: C, 70.37; H, 7.63; N, 10.27. Found: C, 70.30; H, 7.95; N, 9.87. Further elution with pet. ether/

EtOAc/Et₃N, (6:4:0.3) gave 3β-acetoxy-17-(1H-1,2,3-triazol-1-yl) -16-formylandrosta-5,16-diene (Compound 16) (1.48 g, 62%), mp 215–217° C. $^1$H NMR (300 MHz, CDCl₃): δ 1.08 (3H, s, 18-Me), 1.18 (3H, s, 19-Me), 2.04 (3H, s, 3β-OAc), 4.63 (1H, m, 3α-H), 5.43 (1H, d, J=4.2 Hz, 6-H), 7.85 (2H, s, 4' and 5'-H) and 9.94 (1H, s, 16-CHO). Analysis calculated for $C_{24}H_{31}O_3N_3$: C, 70.37; H, 7.63; N, 10.27. Found: C, 70.37; H, 7.86; N, 10.10.

Synthesis Example 14

This Example describes the preparation of 3β-acetoxy-17-(2H-1,2,3-triazol-2-yl) androsta-5, 16-diene (Compound 17).

A mixture of 3β-acetoxy-17-(2H-1,2,3-triazol-2-yl)-16-formylandrosta-5,16-diene (Compound 16) (140 mg, 0.342 mmol) in dry toluene (6.0 ml) and tris (triphenylphoshpine) rhodium (1) chloride (Wilkinson's catalyst,; 332 mg 0.351 mmol) was ref luxed under N₂ for 5 h. After cooling to room temperature, EtOH (12 ml) was added and on further cooling at approx. 0° C., the yellow precipitate of bis (triphenylphosphine)carbonylchloro rhodium(1) formed.

Following filtration, the filtrate was concentrated to give the crude product. This was purified by FCC (silica gel, pet. ether/EtOAc, (15:1)) to give Compound 17, a white solid (120 mg, 92%), mp 154–155° C. $^1$H NMR (300 MHz, CDCl₃): δ 1.09 (3H, s, 18-Me), 1.14 (3H, s, 19-Me), 2.04 (3H, s, 3,B-OAc), 4.60 (1H, m, 3α-H), 5.42 (1H, d, J=4.2 Hz, 6-H), 6.17 (1H, br. s, 16-H) and 7.68 (21, s, 4' and 5'-H). Analysis calculated for $C_{23}H_{31}O_2N_3$: C, 72.40; H, 8.19; N, 11.02. Found: C, 72.16; H, 8.32; N, 10.90.

Synthesis Example 15

This Example describes the preparation of 3β-hydroxy-17-(2H-1,2,3-triazol-2-yl)androsta-5,16-diene (Compound 18), VN/90-1.

The method followed that described in Synthesis Example 4, but using 3β-acetoxy-17-(2H-1,2,3-triazol-2-yl)androsta-5,16-diene (Compound 17) (110 mg, 0.289 mmol). Purification of the crude product by FCC (silica gel, pet. Ether/EtoAc, (3:1)) gave Compound 18 (95 mg, 97.1%) which was crystallized from hexane/EtOAc, mp 176–177° C. $^1$H NMR (300 MHz, CDCl₃): δ 1.09 (3H, s, 18-Me), 1.15 (3H, s, 19-Me), 3.54 (1H, m, 3α-H), 5.39 (1H, d, J=5.1 Hz, 6-H), 6.17 (1H, s, 16-H) and 7.68 (2H, s, 4' and 5'-H). Analysis calculated for $C_{21}H_{29}ON_3$: C, 74.29; H, 8.83; N, 12.38. Found: C, 72.16; H, 8.32; N, 10.90.

Synthesis Example 16

This Example describes the preparation of 3β-acetoxy-17-(1H-1,2,3-triazol-1-yl)androsta-5,16-diene (Compound 19).

The method followed that described for Synthesis Example 3, Method 2, but using 303-acetoxy-17-(1H-1,2,3-triazol-1-yl)-16-formylandrosta-5,16-diene (Compound 16) (2.0 g, 4.89 mmol). Purification of the crude product by FCC (silica gel, pet. ether/EtOAc/Et₃N, (7.7:2:0.3)) gave Compound 19 (1.67 g, 89.9%), mp 158–160° C. $^1$H NMR (300 MHz, CDCl₃): δ 1.09 (3H, s, 18-Me), 1.14 (3H, s, 19-Me), 2.04 (3H, s, 3,8-OAc), 4.60 (1H, m, 3a-H), 5.40 (1H, d, J=4.2 Hz, 6-H), 5.98 (1H, br. s, 16-H) and 7.73 (2H, s, 4' and 5'-H). Analysis calculated for $C_{23}H_{31}O_2N_3$: C, 72.40; H, 8.19; N, 11.02. Found: C, 72.20; H, 8.21; N, 11.00.

Synthesis Example 17

This Example describes the preparation of 3β-hydroxy-17-(1H-1,2,3-triazol-1-yl)androsta-5,16-diene (Compound 20), VN/87-1.

The method followed that described in Synthesis Example 4, but using 3β-acetoxy-17-(1H-1,2,3-triazol-1-yl)androsta-5,16-diene (Compound 19) (1.5 g, 3.94 mmol). The product was recrystallized from EtOAc/MeOH to give Compound 19 (1.20 g, 90%), mp 220–224° C. $^1$H NMR (300 MHz, CDCl₃): δ 1.08 (3H, s, 18-Me), 1.14 (3H, s, 19-Me), 3.54 (1H, m, 3α-H), 5.39 (1H, d, J=4.8 Hz, 6-H), 5.97 (1H, s, 16-H) and 7.72 (2H, s, 4' and 5'-H). Analysis calculated for $C_{21}H_{29}ON_3$: C, 74.29; H, 8.83; N, 12.38. Found: C, 74.10; H, 8.70; N, 12.15.

Synthesis Example 18

This Example describes the preparation of 17-(1H-1,2,3-triazol-1-yl)androsta-4,16-diene-3-one (Compound 21), VN/109-1.

The method followed that described in Synthesis Example 5, but using 3β-hydroxy-17-(1H-1,2,3-triazol-1-yl)-androsta-5,16-diene (Compound 20) (400 mg, 1.18 mmol). Purification of the crude product by FCC (silica gel, CH₂Cl₂/EtOH, (30:1)) gave Compound 21 (358 mg, 90%), mp 118–120° C. $^1$H NMR (300 MHz, CDCl₃): δ 1.17 (3H, s, 18-Me), 1.25 (3H, s, 19-Me), 5.76 (1H, s, 16-H), 5.95 (1H, s, 4'-H), 7.73 (1H, s, 5'-H), and 7.74 (1H, s, 4'-H). Analysis calculated for $C_{21}H_{27}ON_3$:C, 74.73; H, 8.07; N, 12.46. Found: C, 74.65; H, 8.11; N, 12.34.

Synthesis Example 19

This Example describes the preparation of 3β-acetoxy-17- (2H-tetrazol-2-yl) -16-formylandrosta-5, 16-diene (Compound 22) and 3,-Acetoxy-17-(1H-tetrazol-1-yl)-16-formylandrosta-5,16-diene (Compound 23).

The method followed that described for Synthesis Example 7, but using 3β-acetoxy-17-chloro-16-formylandrosta-5,16-diene (Compound 3) (0.5 g, 1.329 mmol), 1H-tetrazole (187 mg, 1.59 mmol) and Li₂CO₃ (287 mg, 3.94 mmol) gave a crude product (520 mg). Flash column chromatography on elution with pet. ether/EtOAc, (5:1), gave firstly 3β-acetoxy-17-(2H-tetrazol-2-yl)-16-formylandrosta-5,16-diene (Compound 22) (92 mg, 28.2%), mp 170–172° C. (decomp.). $^1$H NMR (300 MHz, CDCl₃): δ 1.1 (3H, s, 18-Me), 1.29 (3H, s, 19-Me), 2.04 (3H, s, 36-OAc), 4.62 (1H, m, 3α-H), 5.42 (1H, d, J=4.2 Hz, 6-H), 8.68 (1H, s, 5'-H) and 10.46 (1H, s, 16-CHO). Analysis calculated for C₃H₃%N4: C, 67.28; H, 7.37; N, 13.65. Found: C, 67.15; H, 7.61; N, 13.45. Further elution with p. ether/EtOAc/Et₃N (7:3:0.3) gave 3β-acetoxy-17-(1H-tetrazol-1-yl) -16-formylandrosta-5, 16-diene (Compound 23) (146 mg, 44.6%), mp 196–198° C. (decomp.). $^1$H NMR (300 MHz, CDCl₃): δ 1.09 (3H, s, 18-Me), 1.20 (3H, s, 19-Me), 2.04 (3H, s, 3f-OAc), 4.62 (1H, m, 1S 3α-H), 5.43 (1H, d, J=4.8 Hz, 6-H), 8.93 (1H, s, 5'-H) and 9.92 (1H, s, 16-CHO). Analysis calculated for $C_{23}H_{30}O_3N_4$: C, 67.28; H, 7.37; N, 13.65. Found: C, 67.05; H, 7.65; N, 13.45.

Synthesis Example 20

This Example describes the preparation of 3β-acetoxy-17-(2H-tetrazol-2-yl)androsta-5,16-diene (Compound 24).

The method followed that described for Synthesis Example 14, but using 3β-acetoxy-17-(2H-tetrazol-2-yl)-16-formylandrosta-5,16-diene (Compound 22) (124 mg, 0.302 mmol). Purification of the crude product by FCC (silica gel, pet. ether/EtOAc (10:1)) gave Compound 24 (61 mg, 52.8%), mp 155–156° C. $^1$H NMR (300 MHz, CDCl₃): δ 1.10 (3H, s, 18-Me), 1.17 (3H, s, 19-Me), 2.04 (3H, s, 3β-OAc), 4.62 (1H, m, 3a-H), 5.42 (1H, d, J=4.85Hz, 6-H), 6.46 (1H, s, 16-H) and 8.52 (1H, s, 5'-H). Analysis calculated for $C_{22}H_{30}O_2N_4$: C, 69.07; H, 7.91; N, 14.65. Found: C, 69.01; H, 8.00; N, 14.45.

Synthesis Example 21

This Example describes the preparation of 3β-hydroxy-17-(2H-tetrazol-2-yl)androsta-5, 16-diene (Compound 25), VN/96-1.

The method followed that described for Synthesis Example 4, but using 3β-acetoxy-17-(2H-tetrazol-2-yl)androsta-5,16-diene (Compound 24) (51 mg, 0.134 mmol). Recrystallization of the product from hexane/EtOAc gave Compound 25 (42 mg, 88%), mp 195–198° C. NMR (300 MHz, CDCl$_3$): δ 1.09 (3H, s, 18-Me), 1.17 (3H, s, 19-Me), 3.55 (1H, m, 3α-H), 5.43 (1H, d, J=5.2Hz, 6-H), 6.46 (1H, s, 16-H) and 8.53 (1H, s, 5'-H). Analysis calculated for $C_{20}H_{28}ON_4$: C, 70.54; H, 8.29; N, 16.46. Found: C, 70.51; H, 8.25; N, 16.50.

Synthesis Example 22

This Example describes the preparation of 3β-acetoxy-17-(1H-tetrazol-1-yl)androsta-5,16-diene (Compound 26).

The method followed that described for Synthesis Example 14, but using 3β-acetoxy-17-(1H-tetrazol-1-yl)-16-formylandrosta-5,16-diene (Compound 23) (140 mg, 0.3415 mmol). Purification of the crude product by FCC (silica gel, pet. ether/EtOAc (3:1)) gave Compound 26 (45 mg, 34.5%); $^1$H NMR (300 MHz, CDCl$_3$): δ 1.08 (3H, s, 18-Me), 1.20 (3H, s, 19-Me), 2.04 (3H, s, 3,-OAc), 4.62 (1H, m, 3α-H), 5.42 (1H, d, J=4.6Hz, 6-H), 6.00 (1H, s, 16-H) and 8.93 (1H, s, 5'-H). This compound was not particularly stable at room temp. (TLC evidence) and was used for the subsequent reaction without further characterization.

Synthesis Example 23

This Example describes the preparation of 3β-hydroxy-17- (1H-tetrazol-1-yl) androsta-5,16-diene (Compound 27), VN/95-1.

The method followed that described for Synthesis Example 4, but using 3β-acetoxy-17-(1H-tetrazol-1-yl) androsta-5,16-diene (Compound 26) (36 mg, 0.094 mmol). Recrystallization of the product from hexane/EtOAc gave Compound 27 (28 mg, 87.4%), mp 200–204° C. (decomp.). NMR (300 MHz, CDCl$_3$): δ 1.06 (3H, s, 18-Me), 1.11 (3H, s, 19-Me), 3.54 (1H, m, 3α-H), 5.38 (1H, br. s, 6-H), 6.13 (1H, s, 16-H) and 8.73 (1H, s, 5'-H). Analysis calculated for $C_{20}H_{28}ON_4$: C, 70.54; H, 8.29; N, 16.46. Found: C, 70.55; H, 8.20; N, 16.42.

Synthesis Example 24

This Example describes the preparation of 3β-acetoxy-17-(1H-pyrazol-1-yl) androsta-5,16-diene (Compound 28) and 3,-acetoxy-17α-(1H-pyrazol-1-yl)androsta-5-ene (Compound 29).

(a) Reaction of 3β-acetoxy-17-chloro-16-formylandrosta-5,16-diene (Compound 3) (0.5 g, 1.329 mmol), pyrazole (136 mg, 1.994 mmol) and K$_2$CO$_3$ (551 mg, 3.99 mmol) as described for Synthesis Example 7 after FCC (silica gel, pet. ether/EtOAc, (4:1)) gave a mixture (341 mg, approx. 3:1) of 3β-acetoxy-17-(1H-pyrazol-1-yl) -16-formylandrosta-5,16-diene and 3β-acetoxy-17- (1H-pyrazol-1-yl) androsta-5-ene. This mixture resisted separation by chromatography.

(b) The above mixture (330 mg) was subjected to the decarbonylation reaction as described for Synthesis Example 14 to give a crude product (350 mg). Flash column chromatography on elution with pet. ether/EtOAc, (15:1), gave firstly 3β-acetoxy-17- (1H-pyrazol-1-yl)androsta-5,16-diene (Compound 28) (123 mg, 35%), mp 159–161° C. $^1$H NMR (300 MHz, CDCl$_3$): δ 1.08 (3H, s, 18-Me), 1.11 (3H, s, 19- Me), 2.04 (3H, s, 3β-OAc), 4.62 (1H, m, 3α-H), 5.42 (1H, d, J=5.1 Hz, 6-H), 5.77 (1H, s, 16-H), 6.32 (1H, s, 4'-H), 7.60 (1H, s, 3'-H) and 7.63 (1H, d, J=2.4 Hz, 5'-H). Analysis calculated for $C_{24}H_{32}O_2N_2$: C, 75.74; H, 8.48; N, 7.37. Found: C, 75.94; H, 8.51; N, 7.33. Further elution with pet. ether/EtOAc, (5:1) gave 3β-acetoxy-17α-(1H-pyrazol-1-yl)androst-5-ene (Compound 29) (93 mg, 30%), mp 238–240° C. $^1$H NMR (300 MHz, CDCl$_3$): δ 0.97 (3H, s, 18-Me), 1.08 (3H, s, 19-Me), 2.04 (3H, s, 3β-OAc), 3.24 (1H, dd, J=4.8 Hz, J$_2$=15.6 Hz, 17β-H), 4.62 (11H, m, 3α-H), 5.43 (1H, d, J=5.1 Hz, 6-H), 6.45 (1H, s, 4'-H), 7.70 (1H, d, J=2.4 Hz, 3'-H) and 7.77 (1H, d, J=4.8 Hz, 5'-H). Analysis calculated for $C_{24}H_{34}O_2N_2$: C, 75.34; H, 8.96; N, 7.33. Found: C, 75.24; H, 8.90; N, 7.30.

Synthesis Example 25

This Example describes the preparation of 3β-hydroxy-17-(1H-pyrazol-1-yl)androsta-5,16-diene (Compound 30), VN/97-1.

This method followed that described for Synthesis Example 4, but using 3β-acetoxy-17-(1H-pyrazol-1-yl) androsta-5,16-diene (Compound 25) (100 mg, 0.236 mmol). Recrystallization of the product from hexane/EtOAc gave Compound 30 (85.8 mg, 95.6%), mp 197–199° C.; $^1$H NMR (300 MHz, CDCl$_3$): δ 1.06 (3H, s, 18-Me), 1.09 (3H, s, 19-Me), 3.56 (1H, m, 3α-H), 5.39 (1H, s, 6-H), 5.78 (1H, s, 16-H), 6.31 (1H, s, 4'-H), 7.59 (1H, s, 3'-H) and 7.62 (1H, s, 5'-H). Analysis calculated for $C_{22}H_{32}ON_2$: C, 77.59; H, 9.48; N, 8.32. Found: C, 77.66; H, 9.59; N, 8.21.

Example 1

Evaluation of 17-Azolyl Steroids as Inhibitors of Testicular Human and Rat 17α-hydroxylase/$C_{17,20}$-lyase (17α-lyase) in vitro The potency as inhibitors of P450$_{17α}$ of the 17-azolyl steroids obtained in the above Synthesis Examples was evaluated in human and rat testicular microsomes.

Human testicular microsomes were prepared from human testes (obtained from untreated prostatic cancer patients undergoing orchidectomy in the University of Maryland Hospital and Veterans Hospital), as described in Li et al, *The Prostate*, 26:140–150 (1995).

Rat testicular microsomes were prepared from the testes of adult Sprague-Dawley rats (Charles River Laboratories, weight 200–250 g), as described by Li et al, *J. Med. Chem.*, 39:4335–4339 (1996).

The microsomes were stored at −70° C. until assayed. Just before use, the thawed microsomes were diluted with 0.1 M phosphate buffer (pH 7.4) to appropriate concentrations.

The protein concentration of the microsomes used in the assay was determined by the method of Lowry et al, *J. Biol. Chem.*, 193:265–275 (1951).

The enzyme reaction (activity) was monitored by determination of the release of $C^3H_3COOH$ from [21-$^3H_3$]-17α-hydroxypregnenolone during cleavage of the 30 C-21 side-chain in the conversion to dehydroepiandrosterone (DHEA) as described by Njar et al, *Steroids*, 62:468–473 (1997). This assay measures only the lyase activity of the P450$_{17α}$ enzyme. This assay is comparable to the HPLC assay procedure (which utilizes [7-$^3$H]-pregnenolone as substrate), and measures both the hydroxylase and lyase activities of the enzyme.

The results are presented in Tables 1 and 2 below:

TABLE 1

The Inhibition of Human P450$_{17\alpha}$ by
$\Delta^{16}$-17-Azolyl Steroids

| Compound[a] | % Inhibition[b] |
|---|---|
| 6 (VN/63-1) | 60 |
| 17 (VN/85-1) | 97 |
| 18 (VN/90-1) | N.I.[c] |
| 20 (VN/87-1) | 94 |
| 25 (VN/96-1) | N.I.[c] |
| 27 (VN/95-1) | N.I.[c] |
| 30 (VN/97-1) | 40 |
| for comparison | |
| Ketoconazole | 67 |

[a]Each inhibitor concentration was 150 nM.
[b]Concentration of substrate, 17α-hydroxypregnenolone = 10 μM.
[c]N.I. = No inhibition at concentration of 150 nM.
All values are the mean of two determinations.

TABLE 2

Inhibitory Potency of $\Delta^{16}$-17-Azolyl
Steroids Towards Human and Rat
P450$_{17\alpha}$ and Human Steroid 5α-Reductase

| | Human P450$_{17\alpha}$ | | Rat P450$_{17\alpha}$ | 5α-Reductase |
|---|---|---|---|---|
| Compound | IC$_{50}$ (nM)[a] | K$_i$ (nM)[b,c] | IC$_{50}$ (nM)[a] | IC$_{50}$ (nM)[a] |
| 6 (VN/63-1) | 90 ± 14 | 23 | 26 ± 13 | ~160,000 |
| 7 (VN/107-1) | 55 ± 11 | 41 | 11 ± 3 | 152 ± 10 |
| 8 (VN/111-1) | 219 ± 21 | — | — | — |
| 11 (VN/85-1) | 8 ± 1 | 1.2 | 9 ± 2 | ~400,000 |
| 12 (VN/108-1) | 7 ± 1 | 1.9 | 8 ± 0.7 | 142 ± 5 |
| 13 (VN/112-1) | 62 ± 2 | — | — | — |
| 14 (VN/113-1) | 36 ± 9 | — | — | 765 ± 100 |
| 20 (VN/87-1) | 13 ± 1 | 1.4 | 10 ± 0.4 | ~10,000 |
| 21 (VN/109-1) | 19 ± 1 | 8 | 9 ± 2 | 198 ± 33 |
| for comparison | | | | |
| Ketoconazole | 78 ± 3 | 38 | 209 ± 17 | — |
| Finasteride | — | — | — | 33 ± 2 |

[a]Mean ± SDM of at least two experiments.
[b]K$_i$ values were determined as described herein.
[c]K$_m$ for substrate, 17α-hydroxypregnenolone = 560 nM.

In all experiments, the blank activity ranged from 1–5% of the control activity. IC$_{50}$ values for inhibitors were calculated from the linear regression line in the plot of logit of lyase activity versus log of inhibitor concentration. K$_i$ values were also determined from assays as described by Njar et al (1997), supra. Each inhibitor was examined at three concentrations. Data from the various assays were used to obtain Lineweaver-Burk plots and from replots of slopes versus inhibitor concentration (FIG. 2B), K$_i$ values were obtained and the K$_m$ for 17α-hydroxypregnenolone (substrate) was also determined (Table 2).

In order to estimate the inhibitor potency of the compounds of the present invention, the tritiated substrate, a NADPH generating system and microsomes were incubated at 34° C. in O$_2$ in the presence or absence of the inhibitor. The reaction was usually monitored for 60 min during which time the formation of [$^3$H]-acetic acid, and thus DHEA was linear. The percentage inhibition data for the initial target compounds of this study are presented in Table 1 and highlights that 2H-1,2,3-triazole (Compound 18, VN/90-1) and the two tetrazole regioisomers (Compound 25, VN/96-1; and Compound 27, VN/95-1) were non-inhibitory, while the 1H-pyrazole (Compound 30, VN/97-1) was a moderate inhibitor. By contrast the 1H-1,2,4-triazole (Compound 6, VN/63-1), 1H-imidazole (Compound 11, VN/85-1) and 1H-1,2,3-triazole (Compound 20, VN/87-1) were potent inhibitors of the enzyme. Ketoconazole also showed strong inhibition. Given that these $\Delta^{16}$-17-azole compounds of Table 1 are structurally similar, (i.e., they all possess the $\Delta^5$-3β-ol functionality) the striking difference in the inhibitory properties observed may be due to the differences in their basicities, a property imposed by the inherent different electronic character of each of the azole heterocycles. In addition, the presence of a nitrogen atom at either the 3' or 4' position seems important for potent inhibition of the enzyme.

Figure 2A:
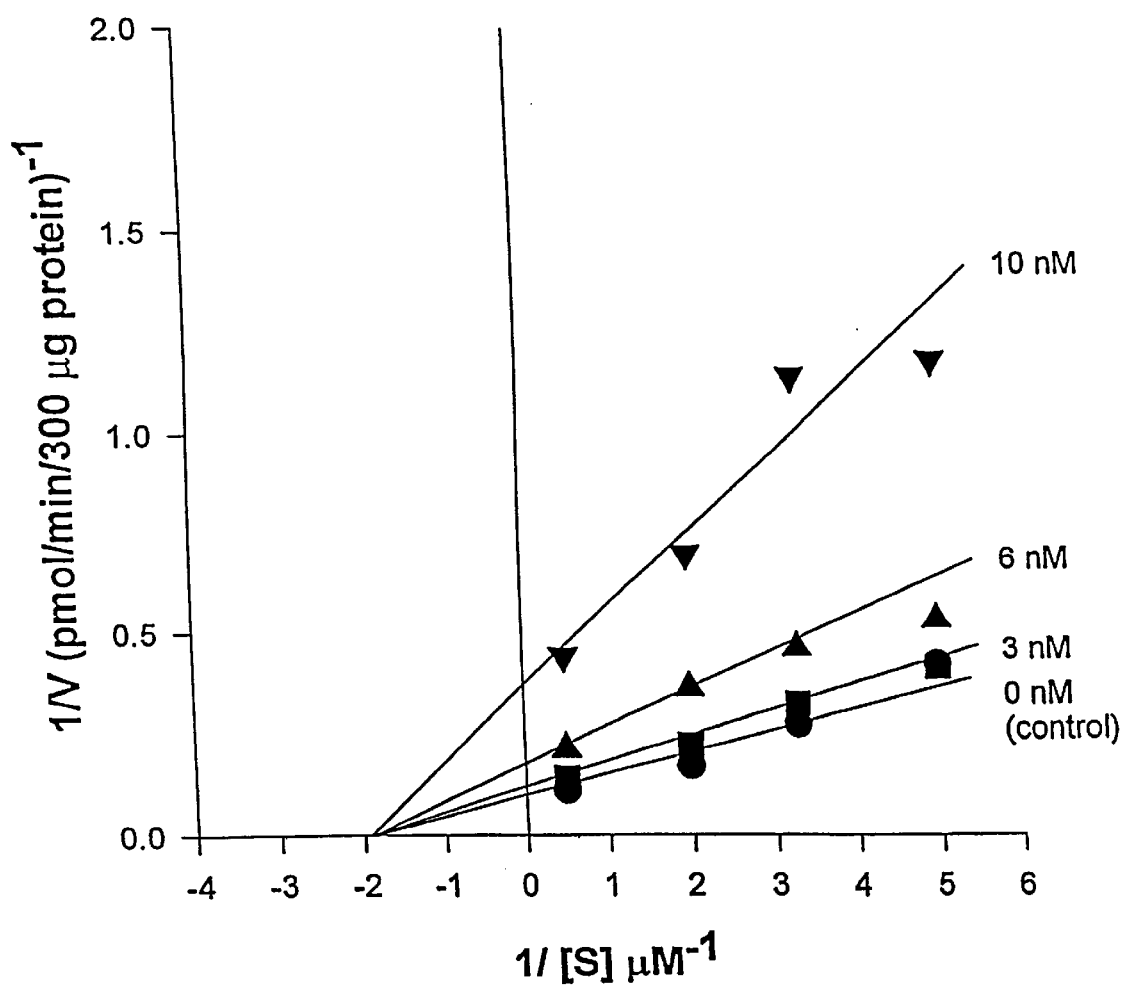
Figure 2B:
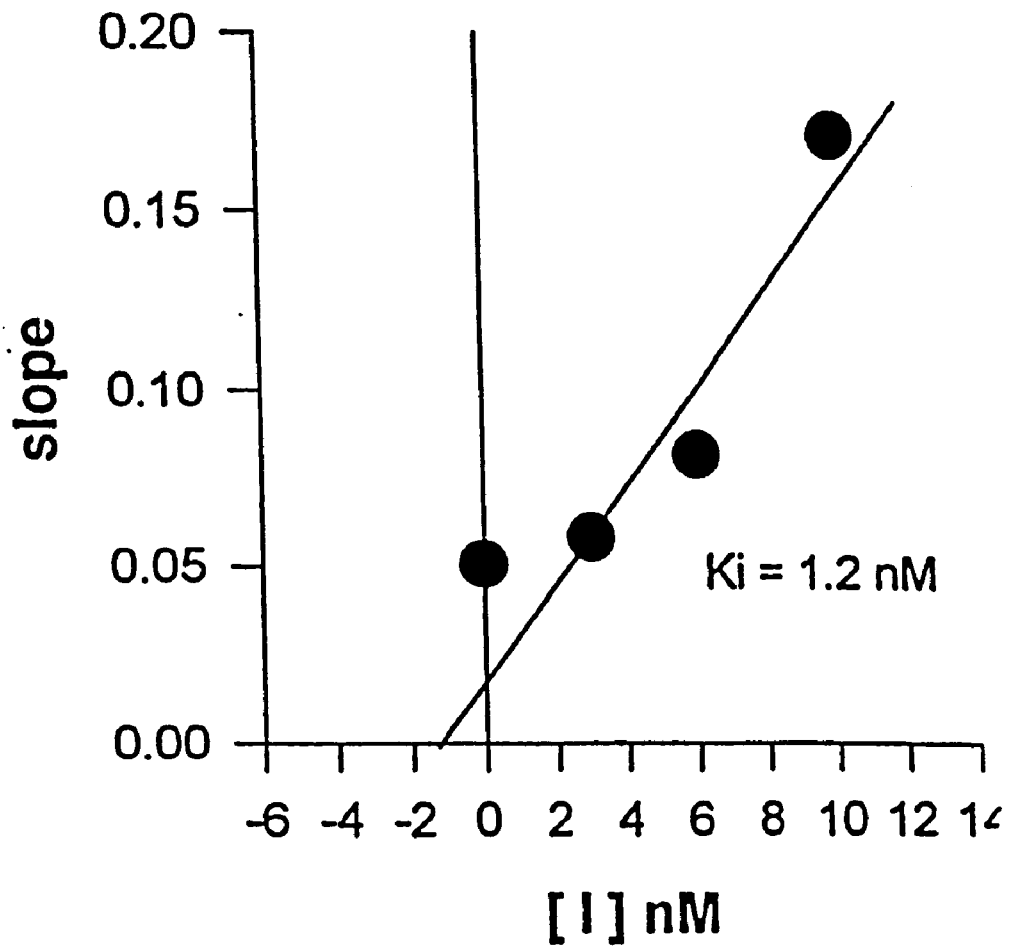
FIG. 2B shows a replot of the slopes of each reciprocal plot versus inhibitor concentration [I] to obtain the $K_i$ value. The inhibition experiments with the other azoles (Compounds 6, 7, 12, 20 and 21) gave plots that were essentially the same as shown herein.

Following the initial screening assays, Compounds 6, 11 and 20 together with their corresponding $\Delta^4$-3-one counterparts, Compounds 7 (VN/107-1), 12 (VN/108-1) and 21 (VN/109-1), respectively, were evaluated further to determine firstly, their IC$_{50}$ values and then their apparent K$_i$ values (from Lineweaver-Burk plots, e.g., FIG. 2A). These values are presented in Table 2. All six 17-azoles are excellent noncompetitive inhibitors of P450$_{17\alpha}$ as shown in the example in FIG. 2A. The nature of inhibition kinetics exhibited by these compounds was that in which the V$_{max}$ was decreased, but the apparent K$_m$ was unchanged; i.e., the intercept on the horizontal axis is the same in the absence or presence of inhibitor. This is one of two characteristics of a noncompetitive inhibitor, and indicates destruction of the catalytic activity of the enzyme. The other is when binding of the inhibitor and (variable) substrate are not mutually exclusive.

There was no marked difference between the inhibitory potencies of the $\Delta^5$-3β-ol azoles (Compounds 6, 11 and 20) with those of the corresponding $\Delta^4$-3-ones (Compounds 7, 12 and 21).

Three of the compounds, i.e., Compounds 7, 12 and 20 with K$_i$ values of 1.2, 1.8 and 1.4 nM, respectively, (K$_m$ of the substrate, 17α-hydroxypregnenolone was 530 nM), were the most potent inhibitors, and they are indeed the most potent inhibitors of human testicular microsomal P450$_{17\alpha}$ described to date. These compounds were 20–32 times more potent as P450$_{17\alpha}$ inhibitors when compared in the same assay with ketoconazole (K$_i$32 38 nM). Some $\Delta^{16}$-17-(3-pyridyl) compounds were recently classified as the most potent inhibitors of this enzyme (Potter et al, supra). However, three of their most potent inhibitors were 9–12 times more potent as P450$_{17\alpha}$ (lyase activity) inhibitors when compared in the same assay with ketoconazole (Potter et al, supra). The requirement of 16,17-double bond was also observed with these P450$_{17\alpha}$ inhibitors: 17β-(1H-1,2,4-triazolyl)- and 17β-(1H-imidazolyl)- compounds, Compounds 8 (VN/111-1) and 13 (VN/112-1) each exhibited diminished potency compared to the corresponding parent $\Delta^{16}$ compounds, Compounds 6 and 11, respectively, (Compound 6→Compound 8, IC$_{50}$ 90→219 nM, and Compound 11→Compound 13, IC$_{50}$ 8→62 nM). A similar observation has been previously reported (Potter et al, supra; Burkhart et al, *Bioorg. Med. Chem.*, 4:1411–1420 (1996); and Ling et al, supra) for a number of $\Delta^{16}$-17-heteroaryl P450$_{17\alpha}$ inhibitors. Conversion of Compound 13 to the $\Delta^4$-3-one compound, Compound 14 resulted in a modest increase in inhibitory activity (62→36 nM).

Figure 3:
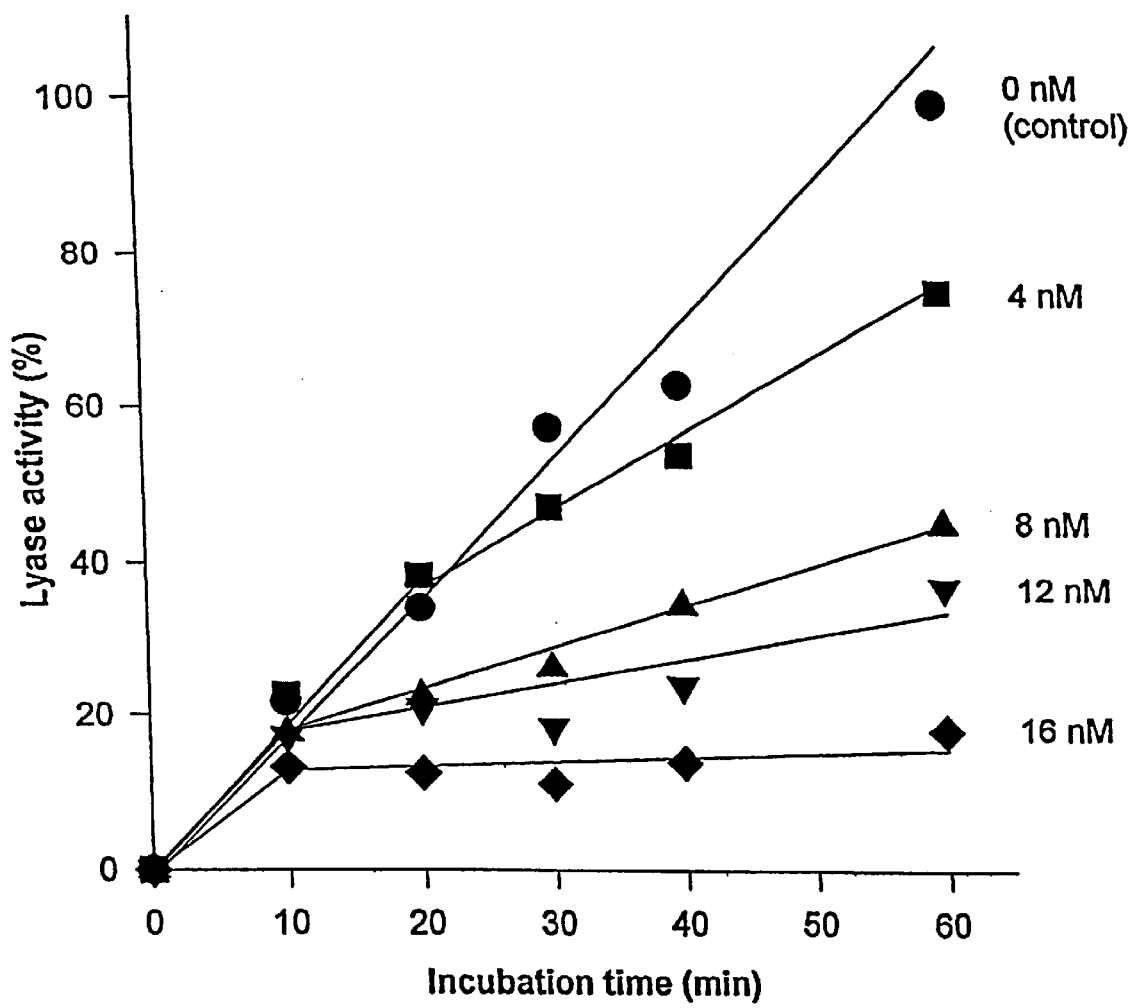
FIG. 3 shows progress curves for the inhibition of human testicular microsomal $P450_{17\alpha}$ by $\Delta^6$-17-(1H-imidazole) (Compound 11) at different 25 concentrations.

When the lyase reaction was monitored in the presence of various concentrations of the imidazole, Compound 11, a family of non-linear progress curves were obtained in which the extent of inhibition increased with time (FIG. 3). This suggest that Compound 11 may be a slow-binding inhibitor (Morrison, et al, *Adv. Enzymol. Relat. Areas Mol. Biol.*, 61:201–301 (1988)). Although the other potent inhibitors were not examined in this assay, it is likely that they may also behave in a similar fashion. Compound 11 appears to be the first example of a slow-binding inhibitor of cytochrome $P450_{17\alpha}$.

Figure 4:
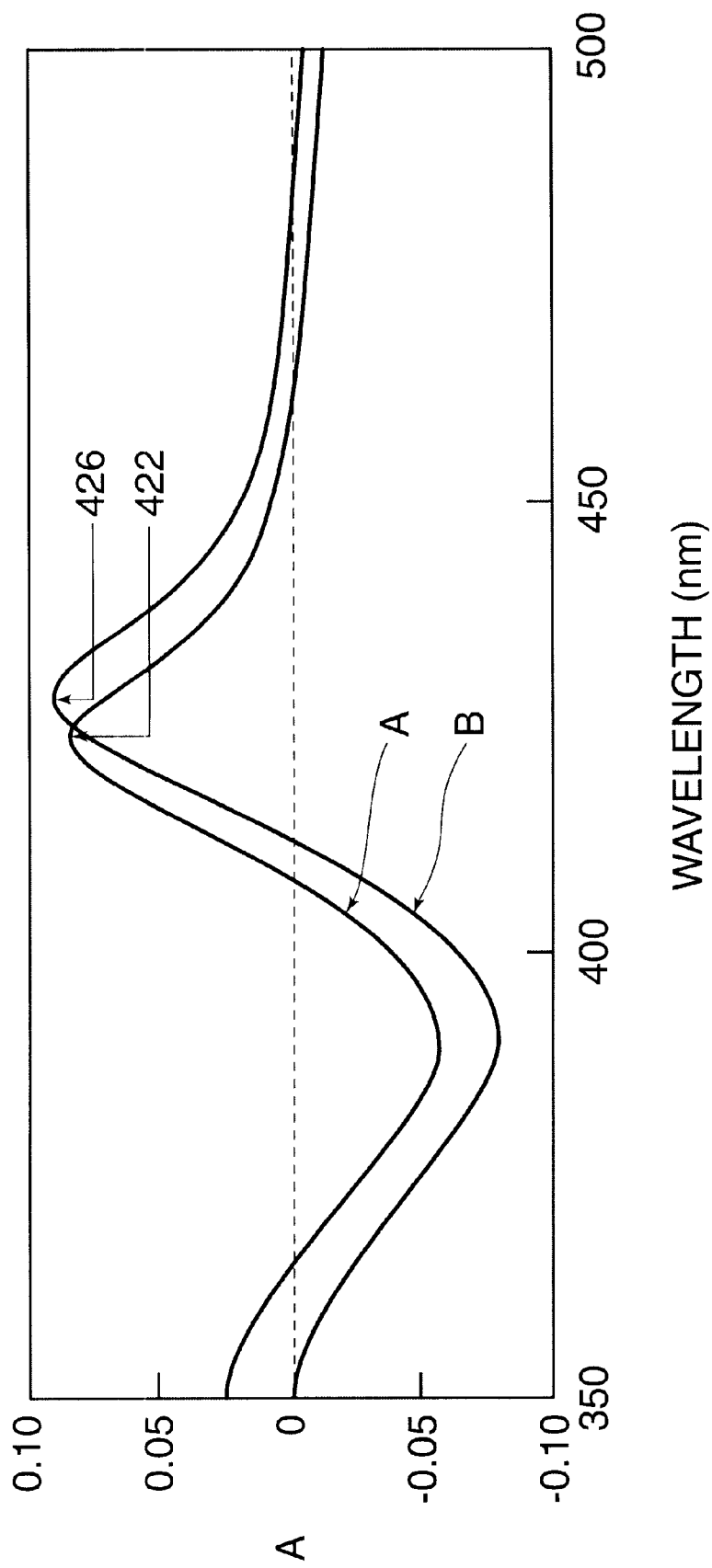
FIG. 4 shows difference absorption spectra, wherein the experimental and reference cuvettes contained a modified form of $P450_{17\alpha}$ (P450 concentration 1.8 μM). The spectra show the effects of addition of 20 μM $\Delta^{16}$-17-(1H-1,2,3-triazole) (Compound 6), (curve A) and 20 μM $\Delta^{16}$-17-(1H-imidazole) (Compound 11), (curve B).

To investigate the mechanism of $P450_{17\alpha}$ inhibition further, the properties (chemical nature) of the complexes formed between the 1H-1,2,4-triazole, Compound 6 and imidazole, Compound 11 and a modified form of human $P450_{17\alpha}$ (Imai et al, *J. Biol. Chem.*, 268:19681–19689 (1993) were next studied using UV-VIS difference spectroscopy as described by Jefcoat, *Methods Enzymol.*, 52:258–279 (1978). Each of these compounds induced a Type II difference spectrum (FIG. 4), indicating coordination of a steroidal nitrogen (probably N-4 of the triazole ring or N-3 of the imidazole ring) to the here iron of the cytochrome P450 enzyme, with formation of low spin iron. The peak positions of the Soret maxima for the complexes with triazole, Compound 6 (422 nm) and imidazole, Compound 11 (426 nm) are in agreement with available data for the binding of nitrogen ligands to cytochrome P450 systems; resulting in complexes with Soret maximum at 421–430 nm (Dawson et al, *J. Biol. Chem.*, 257:3606–3617 (1982)).

The inhibitory potency of (20R)- and (20S)-aziridinyl steroids have recently been reported, and this stems in part from the additional stabilization due to coordination of the heteroatom of their aziridinyl ring to the heme of rat $P450_{17\alpha}$ (Njar et al, *Bioorg. Med. Chem.*, 4:1447–1453 (1996)). The spectroscopic data described above suggest that this may also be the case for the $\Delta^{16}$-17-azole steroids of the present invention. The ability of the steroidal azole nitrogen atom to coordinate with the heme of $P450_{17\alpha}$ indicates that C-17 and C-20 (the sites of enzymatic hydroxylations) can be positioned in close proximity to the heme center when these substrate-like inhibitors are bound to the enzyme. Although it is not certain that these compounds bind in exactly the same manner as the natural substrates, their high binding affinities make a significantly different mode of binding unlikely. It should be noted that although two groups (Potter et al, supra; and Burkhart et al, supra) have recently reported on 17-heteroaryl steroidal inhibitors of $P450_{17\alpha}$, and believe that the inhibitory property of their compounds are due (in part) to coordination of a heteroaryl atom to the heme-iron of the enzyme complex, they are yet to provide evidence for this phenomenon.

Before evaluating these potent inhibitors in vivo in rodent models as potential therapeutic agents for the treatment of prostate cancer, the potency of these inhibitors was also accessed towards the rat testicular microsomal $P470_{17\alpha}$. A comparison was made between the inhibitory activity, expressed as $IC_{50}$ values, displayed by the $\Delta^5$-3$\beta$-ols, Compounds 6, 11 and 20; the $\Delta^4$-3-one compounds, Compounds 7, 12 and 21, and ketoconazole towards $P470_{17\alpha}$ located in human and rat testicular microsomes. The results are presented in Table 2 and show that whereas the potencies of Compounds 6, 7 and 21 each increased towards the rat enzyme by 3.5-, 5- and 2-folds, respectively, the potencies of Compounds 11, 12 and 20 were unchanged, while that for ketoconazole decreased by about 3-fold. The most potent inhibitors, Compounds 11, 12 and 20 appear to be the first examples of inhibitors that are equipotent towards the human as well as the rat $P450_{17\alpha}$ enzymes. This finding indicates that results from pre-clinical in vivo studies with rats are likely to reflect the clinical situation.

Example 2

Evaluation of 17-Azolyl Steroids as Inhibitors of 5α-Reductase

The effects of the compounds of the present invention and finasteride (a potent inhibitor of this enzyme) on human prostate 5α-reductase activity was evaluated essentially as described by Li et al 1996, supra; and Klus et al, *Cancer Res.*, 56:4956–4964 (1996).

More specifically, ethanolic solutions of [7-$^3$H]-testosterone (600,000 dpm), cold testosterone (4.8 ng), indicated inhibitors (0–200 nM) and propylene glycol (10 μl) were added to sample tubes in duplicate. The ethanol was evaporated to dryness under a gentle stream of air. The samples were reconstituted in 400 μl of 0.1 M phosphate buffer (pH 7.4) containing 78 μM DTT and the NADPH generating system comprising 6.5 mM NADP; 71 mm glucose-6-phosphate, and 2.5 IU glucose-6-phosphate dehydrogenase in 100 μl of phosphate buffer, was added to each tube. The tubes were preincubated at 37° C. for 15 min. The enzymatic reactions were initiated by addition of human BPH microsomes (about 180 μg of microsomal protein in 500 μl of phosphate buffer) in a total volume of 1.0 ml, and the incubations were performed for 10 min under oxygen in a shaking water bath at 37° C. The incubations were terminated by placing the sample tubes on ice and the addition of ether. Also, [$^{14}$C]-DHT (3000 dpm) and cold DHT (50 μg) were added to each tube as an internal standard and visualization marker, respectively. The steroids were extracted with ether and separated by TLC (chloroform:ether, 80:20) and visualized by exposure to iodine vapor. The extracts were analyzed for $^3$H and $^{14}$C using a liquid scintillation counter. The percentage conversion of [7-$^3$H]-testosterone to [$^3$H]-dihydrotestosterone was calculated and used to determine 5α-reductase activity. $IC_{50}$ values were determined from plots of 5α-reductase activity against four different concentrations of the inhibitor.

The results are presented in Table 2 and highlights that the $\Delta^5$-3$\beta$-ol compounds (Compounds 6, 11 and 20) were poor inhibitors of the enzyme. By contrast, the corresponding $\Delta^4$-3-one compounds (Compounds 7, 12 and 21) were potent inhibitors, being only about 4–6 times less potent than finasteride, a potent 5α-reductase inhibitor currently used in the treatment of benign prostatic hyperplasia.

Example 3

The Effect of Inhibitors on Androgen-dependent Growth of Human Prostate Cancer (LNCaP) Cells in vitro The abilities of Compounds 11 and 20 to inhibit the androgen-stimulated growth of LNCaP human prostatic cancer cell were examined. As previously reported by Klus et al, supra, 0.1 nM testosterone increased the growth of these LNCaP cells 6-fold compared to vehicle-treated cells, and 30 μM DHT stimulated proliferation 5-fold compared to control. The imidazole, Compound 11 was more effective than Compound 20 in inhibiting the testosterone-stimulated growth of LNCaP cells, with 100% inhibition occurring at 1.0 and 2.5 μM, respectively. Both compounds also inhibited DHT-induced cell growth with Compound 11 again being more effective (100% inhibition at 2.5 and 5.0 μM, respectively). Since neither compound inhibited 5α-reductase nor was toxic to the cells in the concentration range 0.5–5.0 μM, these results indicate that their growth-inhibiting properties are due to possible anti-androgenic effects.

In summary, the present invention describes a method for the introduction of a variety of azolyl groups at the 17-carbon of a $\Delta^{16}$ steroid. This enabled the synthesis of several $\Delta^{16}$-17-azolyl steroids of which Compounds 6, 7, 11, 12, 20, and 21 proved to be powerful inhibitors of both human and rat testicular $P450_{17\alpha}$. In addition, it is shown that a nitrogen of Compound 6 and 11, each coordinates to the enzyme's heme-iron. Kinetic studies allowed for classification of these compounds as noncompetitive inhibitors of the enzyme. Unlike most previously described $P450_{17\alpha}$ inhibitors which show normal competitive or noncompetitive reversible kinetics, the most potent inhibitor, Compound 11 shows an apparent slow binding behavior. Compounds 12, 20 and 21 are also potent inhibitors of 5α-reductase, while Compounds 11 and 20 appear to possess strong antiandrogenic effects. These dual biological properties of some of these compounds increase their utility in the treatment of prostate cancer.

While the invention has been described in detail, and with reference to specific embodiments thereof, it will be apparent to one of ordinary skill in the art that various changes and modifications can be made therein without departing from the spirit and scope thereof.

What is claimed:

1. A compound of general Formula (I):

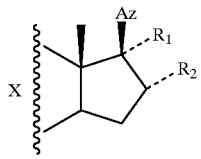

wherein X represents the residue of the A, B and C rings of a 6-azasteroid consisting of a 4-en-3-one or 5-en-3β-ol system; Az represents an azole ring attached to C-17 of the steroid via a hetero nitrogen atom; and $R_1$ and $R_2$ represent a hydrogen atom or together represent a double bond.

2. The compound of claim 1, where Az is selected from the group consisting of

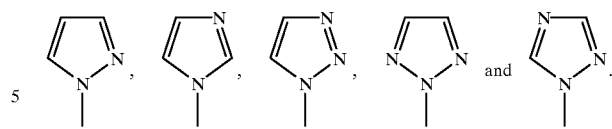

3. The compound of claim 1, wherein said steroid further comprises a basic structure selected from the group consisting of $\Delta^4$-3-one, $A^5$-3β-ol and $\Delta^{14}$-3-one.

4. A pharmaceutical composition comprising of at least one compound according to claim 1; and a pharmaceutically acceptable carrier or diluent.

5. A method for reducing plasma levels of testosterone and/or dihydrotestosterone (DHT) in a subject in need of such treatment comprising administering to said subject at least one compound according to claim 1 in an amount sufficient to reduce plasma levels of testosterone and/or DTH.

6. A method for treating benign prostatic hyperblasia in a subject in need of such treatment comprising administering to said subject at least one compound according to claim 1 in an amount sufficient to reduce the size of the prostate.

7. A method for treating prostate cancer in a subject in need of such treatment comprising administering to said subject at least one compound according to claim 1 in an amount sufficient to reduce the size of the prostate tumors.

* * * * *